United States Patent
Kong et al.

(10) Patent No.: US 10,752,631 B2
(45) Date of Patent: Aug. 25, 2020

(54) HETEROCYCLIC COMPOUNDS AS FGFR INHIBITORS

(71) Applicant: GUANGZHOU INNOCARE PHARMA TECH CO., LTD., Guangzhou (CN)

(72) Inventors: Norman Xianglong Kong, Nanjing (CN); Chao Zhou, Nanjing (CN); Xiangyang Chen, Beijing (CN)

(73) Assignee: Guangzhou Innocare Pharma Tech Co., Ltd., Guangzhou, Guangdong (CN)

( * ) Notice: Subject to any disclaimer, the term of this patent is extended or adjusted under 35 U.S.C. 154(b) by 11 days.

(21) Appl. No.: 16/324,189

(22) PCT Filed: Jul. 27, 2017

(86) PCT No.: PCT/CN2017/094620
§ 371 (c)(1),
(2) Date: Feb. 8, 2019

(87) PCT Pub. No.: WO2018/028438
PCT Pub. Date: Feb. 15, 2018

(65) Prior Publication Data
US 2019/0177333 A1    Jun. 13, 2019

(30) Foreign Application Priority Data

Aug. 9, 2016  (CN) .......................... 2016 1 0647295

(51) Int. Cl.
| | | |
|---|---|---|
| *C07D 487/04* | (2006.01) | |
| *C07D 471/04* | (2006.01) | |
| *A61P 35/04* | (2006.01) | |
| *A61P 35/00* | (2006.01) | |
| *A61K 31/525* | (2006.01) | |
| *A61K 31/437* | (2006.01) | |

(52) U.S. Cl.
CPC .......... *C07D 487/04* (2013.01); *A61K 31/437* (2013.01); *A61K 31/525* (2013.01); *A61P 35/00* (2018.01); *A61P 35/04* (2018.01); *C07D 471/04* (2013.01)

(58) Field of Classification Search
CPC ... C07D 487/04; C07D 4714/04; A61P 35/04; A61P 35/00; A61K 31/437; A61K 31/525
See application file for complete search history.

(56) References Cited

U.S. PATENT DOCUMENTS 9,108,973 B2    8/2015 Sagara et al.

FOREIGN PATENT DOCUMENTS

| CN | 103958512 A | | 7/2014 | |
|---|---|---|---|---|
| EP | 3 023 100 | * | 5/2016 | ........... A61K 31/437 |
| EP | 3023100 A1 | | 5/2016 | |
| WO | 2007087395 A2 | | 8/2007 | |

OTHER PUBLICATIONS

International Search Report and Written Opinion for International Application No. PCT/CN2017/094620 dated Oct. 19, 2017, 9 pages.
Extended European Search Report for European Application No. 17 838 568.8, dated Jan. 28, 2020, 5 pages.

* cited by examiner

*Primary Examiner* — Erich A Leeser
(74) *Attorney, Agent, or Firm* — RatnerPrestia

(57) ABSTRACT

The present invention relates to a heterocyclic compound, a pharmaceutical composition containing the same, a preparation method thereof, and a use thereof as a fibroblast growth factor receptor (FGFR) inhibitor. The compound is a heterocyclic compound as shown in Formula I, or a pharmaceutically acceptable salt, a prodrug, a solvate, a polymorph, an isomer, or a stable isotopic derivative thereof. The present invention further relates to a method of treating or preventing a FGFR-mediated disease, such as cancer, using the compound.

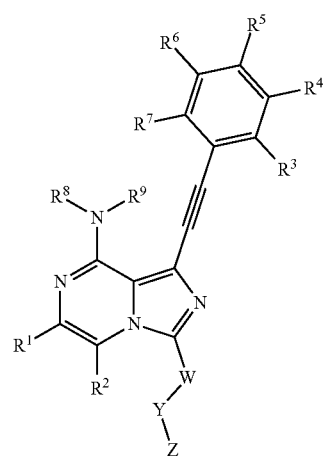

(I)

20 Claims, No Drawings

HETEROCYCLIC COMPOUNDS AS FGFR INHIBITORS

The present application is a U.S. National Phase Application of International Application PCT/CN2017/094620, filed Jul. 27, 2017, which claims the benefit of Chinese Patent Application No. CN 201610647295.0 filed on Aug. 9, 2016, the contents of each of which are incorporated herein in their entireties for all purposes.

TECHNICAL FIELD

The present invention relates to a heterocyclic compound, a preparation method of a pharmaceutical composition containing the same, and a use thereof as a fibroblast growth factor receptor (FGFR) inhibitor. The compound according to the present invention can be used to treat or prevent related diseases mediated by FGFR, such as cancer.

BACKGROUND ART

Fibroblast Growth Factor Receptor (FGFR) belongs to receptor tyrosine kinases. FGFR mainly comprises four members: FGFR1, FGFR2, FGFR3 and FGFR4. FGFRs participate and regulate cell proliferation, migration, apoptosis, angiogenesis and many other processes. For their wide functions, FGFRs and other RTKs are strictly regulated under normal conditions. In tumors, such as liver cancer, bladder cancer, lung cancer, breast cancer and prostate cancer, FGFR activation mutation or ligand/receptor overexpression would cause their continuous constitutive activation. It is not only closely related to the occurrence, development and poor prognosis of tumors, but also plays an important role in neovascularization, invasion and metastasis of tumors. Therefore, FGFR was regarded as the important target for antitumor therapy. The development of small molecule inhibitors of FGFR has attracted more and more attention.

The binding of Fibroblast Growth Factor (FGF) to FGFR would cause phosphorylation activation of tyrosine residues or target protein tyrosine residues in receptor intracellular segment. And then activated related transduction pathways through a variety of intracellular signal transducers. At present, it is shown that the downstream cascade signaling pathways induced by FGF include: (1) PKC pathway; (2) Ras/Raf/MEK/Erk pathway; (3) JAK/STAT pathway; (4) PI3K pathway. Interestingly, FGF signaling can activate protein kinases Erk1 and Erk2, and the duration of kinase activity is obviously longer than that of phosphorylated kinase induced by epidermal growth factor (EGF); activation of different pathways can also phosphorylate early transcription factors such as Myc and Fos to promote the transcription of related target genes; at the same time, phosphorylated FGFR can play a role in the directly transfect into the nucleus.

Mutations in FGFR 1 can lead to three genetic diseases: KaLIman syndrome, Pfeiffer syndrome and Osteoglophonic dysplasia. FGFR1 signaling abnormalities were also found in some tumors. It was found that there is highly-expressed FGFR1 in breast cancer, glioma, hepatocellular carcinoma cell. Moreover, abnormal signal transduction mediated by FGFR1 is closely related to fibrotic diseases such as pulmonary fibrosis and cirrhosis of the liver. Studies also found that the mutation of FGFR1 was associated with non-small cell lung cancer and squamous cell lung cancer. Of more than 20 different fibroblast growth factors discovered, FGFR1 can bind to more than 10 different fibroblast growth factors, but preferentially bind to FGF 1 (acidic fibroblast growth factor) and FGF 2 (basic fibroblast growth factor). They have the biological activities of stimulating the growth of fibroblasts, vascular endothelial cells, smooth muscle cells and nerve cells. FGFR1 is their high affinity receptor. When FGF binds to the extracellular segment of FGFR1, the tyrosine kinase active region in the receptor cell segment first phosphorylates itself, then transphosphorylates the receptor target protein, and transmits the ligand signal to the nucleus through protein cascade reaction, which is manifested in promoting injury repair, embryonic development, bone formation, angiogenesis and nerve regeneration.

FGFR2 plays an important role in embryonic development and tissue repair. It also plays a more significant role in bone and angiogenesis. It was also found that it is closely related to tumor angiogenesis, tumor staging, metastasis, prognosis and chemotherapy efficacy. It is over expressed, gene amplificated or missense mutated in many human malignant tumors, such as gastric cancer, lung cancer, breast cancer, ovarian cancer and endometrial cancer. In chronic inflammation, smoking, excessive calorie intake and reduced exercise, the uncontrolled signal of FGFR2 leads to the accumulation of epigenetic modification and gene variation, which causes cancer. FGFR2 is the basis of invasive characteristics of advanced gastric cancer, which is closely related to the pathological type, clinical stage, lymph node and distant metastasis of gastric cancer. FGFR2 has high affinity with many different FGFs. However, the selective splicing of the extracellular region mRNA of FGFR2 makes the C-terminus of the region highly variable, producing two subtypes of high affinity FGFR 2-IIIb or FGFR 2-IIIc with transmembrane structure. FGFR2-IIIb is mainly expressed in epithelial cells, and FGFR2-IIIc is mainly expressed in interstitial cells. FGF7 and FGF10 expressed in stromal cells can specifically activate FGFR2-111b. FGF10 has a higher affinity with FGFR2IIIb and is a specific ligand of FGFR2IIIb. FGF2, FGF4, FGF6, FGF8, FGF9 specifically active FGFR2-IIIc. It was found that FGF7 secreted from gastric stromal cells could promote the growth of gastric cancer cells. The more malignant the cells were, the higher the expression of FGFR2-IIIb was. There was no expression of FGFR in gastric stromal fibrosis cells. Many studies around the molecules of FGFR2 have shown that monoclonal antibodies against FGFR2 have significant inhibitory effects on the high expression or activation of FGFR2 in gastric cancer cells. Combined chemotherapy has synergistic effects on the inhibition of gastric cancer. It shows that FGFR2 is potential good target for the treatment of advanced gastric cancer.

Fibroblast growth factor receptor 3 (FGFR3) not only plays an important role in the development of skeleton, articular cartilage and the maintenance of articular chondrocyte homeostasis, but also plays an important role in osteoarthritis. It has been found that mutation activation of FGFR3 gene can lead to a series of hereditary skeletal development defects, such as fatal dwarfism, achondroplasia, cranial suture premature closure syndrome. Recently, anti-tumour studies have found mutations in FGFR3 gene in multiple myeloma, cervical cancer and bladder cancer, especially in primary and lymph node metastasis bladder cancer. Different mRNA splicing mechanisms in the extracellular domain of FGFR3 produce different FGFR3 receptor homologues, such as: FGFR3a, FGFR3b and FGFR3c. These homologues differ in their selectivity, affinity and tissue expression for ligand binding. For example, FGFR3b is the major form of human epithelial cells and is also the major mutation found in bladder cancer. Of the 23 kinds of FGFs found, FGF9 and FGF18 are relatively specific ligands of FGFR3b. Therefore, targeting-FGFR3 therapies may bring a glimmer of light to bladder cancer patients.

FGFR4 is the major FGF receptor subtype in the liver. Ten of the more than 20 different kinds of fibroblast growth factors (FGF) have been found to bind to FGFR4, of which only FGFR19 binds specifically to FGFR4. Recent studies have shown that changes in FGFR4, such as overexpression, mutation, translocation, and truncation, are associated with the progression of many cancers, including rhabdomyosarcoma, renal cell carcinoma, myeloma, breast cancer, gastric cancer, colon cancer, bladder cancer, pancreatic cancer and hepatocellular carcinoma.

Therefore, it can be predicted that compounds that inhibit FGFR can be used to treat and prevent FGFR-mediated related diseases, such as cancer, including liver cancer (especially hepatocellular carcinoma), bladder cancer, lung cancer, breast cancer, prostate cancer, rhabdomyosarcoma, renal cell cancer, myeloma, gastric cancer and colon cancer.

CONTENTS OF THE INVENTION

The present invention is to provide as FGFR inhibitor a compound as shown in Formula I, or an isomer, a prodrug, a stable isotopic derivative and a pharmaceutically acceptable salt thereof:

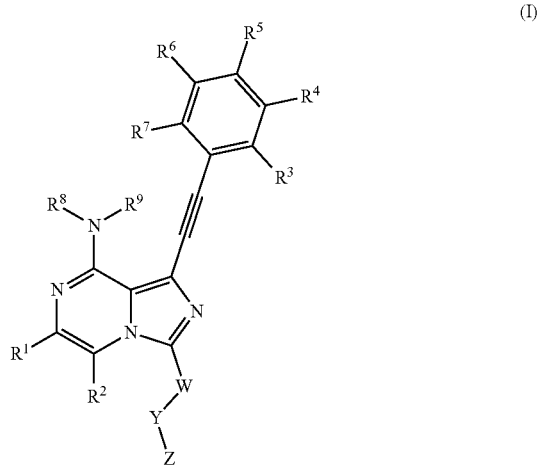

(I)

Where $R^1$, $R^2$ are each independently selected from the group consisting of hydrogen, C1-C6 alkyl, halogen and —CN;

$R^3$, $R^4$, $R^5$, $R^6$, $R^7$ are selected from the group consisting of hydrogen, halogen, C1-C6 alkyl, C3-C8 cyclyl, C2-C6 alkynyl, —$OR^{10}$, —$C(O)NR^{10}R^{11}$, $R^8$, $R^9$ are each independently selected from hydrogen, C1-C6 alkyl;

W is C1-C6 alkyl or absent;

Y is absent or selected from the group consisting of C3-C8 cyclyl, 3-8-membered heterocylcyl, aryl or heteroaryl, where said cyclyl, heterocylyl, aryl and heteroaryl are optionally substituted by one or more $G_1$;

Z is independently selected from —CN, $NR^{12}CN$,

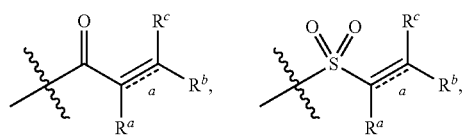

-continued

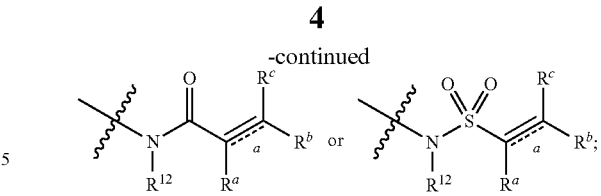

Bond a is a double bond or a triple bond;

When bond a is a double bond, $R^a$, $R^b$ and $R^c$ are each independently selected from the group consisting of hydrogen, —CN, halogen, C1-C6 alkyl, C3-C8 cyclyl or 3-8-membered heterocyclyl, where said alkyl, cyclyl and heterocyclyl are optionally substituted by one or more $G^2$;

$R^a$ and $R^b$ or $R^b$ and $R^c$ may form a ring containing a heteroatom together with the carbon atoms to which they are attached;

When bond a is a triple bond, $R^a$ and $R^c$ are absent, $R^b$ is independently selected from the group consisting of H, C1-C6 alkyl, C3-C8 cyclyl, or 3-8-membered heterocyclyl, where said alkyl, cyclyl, and heterocyclyl are optionally substituted by one or more $G^3$;

$R^{10}$, $R^{11}$ and $R^{12}$ are independently selected from the group consisting of H, C1-C6 alkyl, C3-C8 cyclyl or 3-8-membered heterocyclyl, where said alkyl, cyclyl and heterycyclyl are optionally substituted by one or more $G^4$, $G^1$, $G^2$, $G^3$, $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$, where said alkyl, alkenyl, alkynyl, cyclyl, heterocyclyl, aryl and heteroaryl are optionally substituted by one or more substituents selected from the group consisting of halogen, —CN, C1-C8 alkyl, C3-C8 cyclyl, 3-8-membered heterocyclyl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$;

$R^{13}$, $R^{14}$ and $R^{15}$ are each independently selected from the group consisting of H, C1-C6 alkyl, 2-6-membered heteroalkyl, C3-C8 cyclyl, 3-8-membered monocyclic heterocylcyl, monocyclic heteroaryl or monocyclic aryl, and m is 1 or 2.

In an embodiment of the present invention, a compound as shown general formula (I), an isomer, a prodrug, a stable isotopic derivative thereof or a pharmaceutically acceptable salt thereof is provided, characterized in that the compound as shown in Formula I is of Formula II;

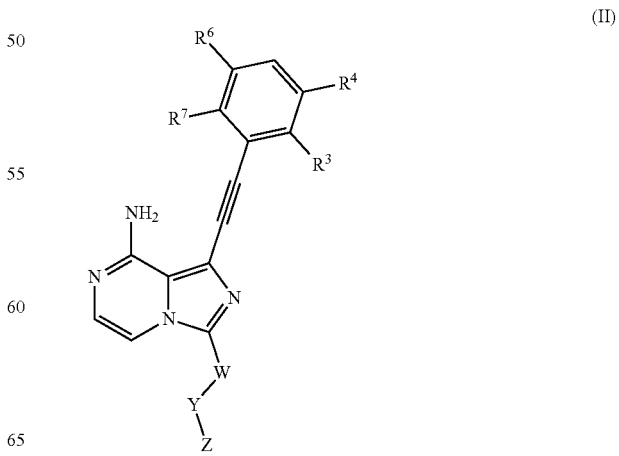

(II)

$R^3$, $R^4$, $R^6$, $R^7$ are selected from the group consisting of hydrogen, halogen, C1-C6 alkyl, C3-C8 cyclyl, C2-C6 alkynyl, —$OR^{16}$, —$C(O)NR^{16}R^{11}$, —$NR^{10}R^{11}$;

W is C1-C6 alkyl or absent;

Y is absent or selected from the group consisting of C3-C8 cyclyl, 3-8-membered heterocyclyl, aryl or heteroaryl, Where said cyclyl, heterocyclyl, aryl, and heteroaryl are optionally substituted by one or more $G^1$;

Z is independently selected from —CN, $NR^{12}CN$,

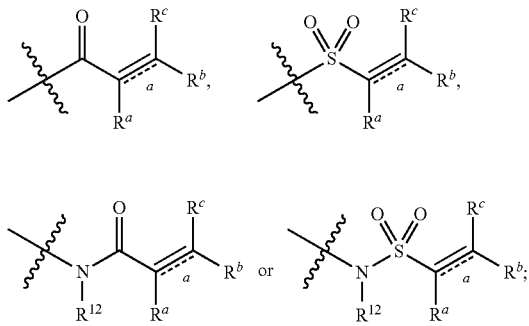

Bond a is a double bond or a triple bond;

When bond a is a double bond, $R^a$, $R^b$ and $R^c$ are each independently selected from the group consisting of H, —CN, halogen, C1-C6 alkyl, C3-C8 cyclyl or 3-8-membered heterocyclyl, where said alkyl, cyclyl and heterocyclyl are optionally substituted by one or more $G^2$;

$R^a$ and $R^b$ or $R^b$ and $R^c$ may form a ring containing a hetero atom together with the carbon atoms to which they are attached;

When bond a is a triple bond, $R^a$ and $R^c$ are absent, $R^b$ is independently selected from the group consisting of H, C1-C6 alkyl, C3-C8 cyclyl or 3-8-membered heterocyclyl, where said alkyl, cyclyl and heterocyclyl are optionally substituted by one or more $G^3$;

$R^{10}$, $R^{11}$ and $R^{12}$ are independently selected from the group consisting of H, C1-C6 alkyl, C3-C8 cyclyl or 3-8-membered heterocyclyl, where said alkyl, cyclyl, and heterocyclyl are optionally substituted by one or more $G^4$;

$G^1$, $G^2$, $G^3$, $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$, where said alkyl, alkenyl, alkynyl, cyclyl, heterocyclyl, aryl, and heteroaryl are optionally substituted by one or more substituents selected from the group consisting of halogen, —CN, C1-C8 alkyl, C3-C8 cyclyl, 3-8-membered heterocyclyl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$;

$R^{13}$, $R^{14}$ and $R^{15}$ are each independently selected from the group consisting of H, C1-C6 alkyl, 2-6-membered heteroalkyl, C3-C8 cyclyl, 3-8-membered monoheterocyclyl, monocyclic heteroaryl or monocyclic aryl; and m is 1 or 2.

In another embodiment of the present invention, a compound as shown in general formula (I), an isomer, a prodrug, a stable isotopic derivative thereof or a pharmaceutically acceptable salt thereof is provided, characterized in that the compound as shown in Formula I is of Formula III;

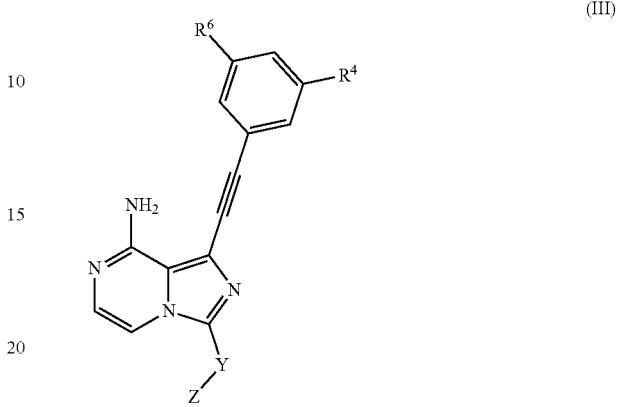

$R^4$, $R^6$ are selected from the group consisting of hydrogen, halogen, C1-C6 alkyl, C3-C8 cyclyl, C2-C6 alkynyl, —$OR^{10}$, —$C(O)NR^{10}R^{11}$, —$NR^{10}R^{11}$;

Y is selected from 3-7 membered heterocyclyl, where said heterocyclyl may be substituted by one or more $G^1$;

Z is independently selected from

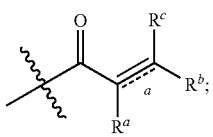

Bond a is a double bond or a triple bond;

When bond a is a double bond, $R^a$, $R^b$ and $R^c$ are each independently selected from the group consisting of H, —CN, halogen, C1-C6 alkyl, C3-C8 cyclyl, 3-8-membered heterocyclyl, where said alkyl, cyclyl, and heterocyclyl are optionally substituted by one or more $G^2$;

$R^a$ and $R^b$ or $R^b$ and $R^c$ may form a ring containing a hetero atom together with the carbon atoms to which they are attached;

When bond a is a triple bond, $R^a$ and $R^b$ are absent, $R^b$ is independently selected from the group consisting of H, C1-C6 alkyl, C3-C8 cyclyl or 3-8-membered heterocyclyl, where said alkyl, cyclyl and heterocyclyl are optionally substituted by one or more $G^3$;

$R^{10}$ and $R^{11}$ are independently selected from the group consisting of H, C1-C6 alkyl, C3-C8 cyclyl or 3-8-membered heterocyclyl, where said alkyl, cyclyl, and heterocyclyl are optionally substituted by one or more $G^4$;

$G^1$, $G^2$, $G^3$, $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$; —$NR^{13}C(O)R^{14}$; —$NR^{13}C(O)NR^{13}R^{14}$, —$S(O)_mR^{13}$ or —$NR^{13}S(O)_mR^{14}$, where said alkyl, alkenyl, alkynyl, cyclyl, 3-8-membered heterocyclyl, aryl or heteroaryl are optionally substituted by one or more substituents selected from the group consisting of halogen, —CN, C1-C8 alkyl, C3-C8 cyclyl, 3-8-membered heterocyclyl, —OR$^{13}$, —OC(O)NR$^{13}$R$^{14}$, —C(O)OR$^{13}$, —C(O)NR$^{13}$R$^{14}$, —C(O)R$^{13}$, —NR$^{13}$R$^{14}$; —NR$^{13}$C(O)R$^{14}$, —NR$^{13}$C(O)NR$^{14}$R$^{15}$, —S(O)$_m$R$^{13}$ or —NR$^{13}$S(O)$_m$R$^{14}$;

R$^{13}$, R$^{14}$ and R$^{15}$ are each independently selected from the group consisting of H, C1-C6 alkyl, 2-6-membered heteroalkyl, C3-C8 cyclyl, 3-8-membered monocyclic heterocylcyl, monocyclic heteroaryl or monocyclic aryl; and m is 1 or 2.

The preferred compounds according to the present invention include, but not limited to:

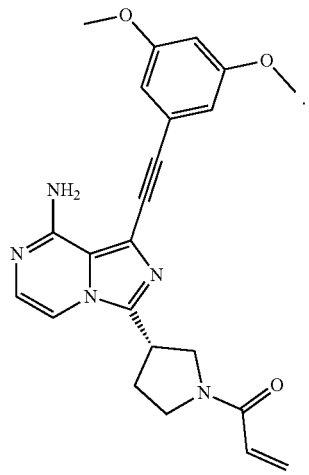

(S)-1-((3,5-Dimethoxyphenyl)ethynyl)-3-(1-acrylpyrrolidin-3-yl)imidazo[1,5-α]pyrazin-8-amine

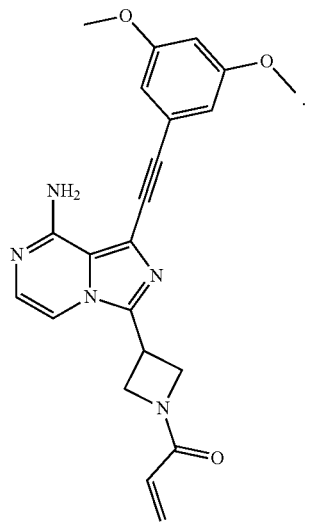

1-((3,5-Dimethoxyphenyl)ethynyl)-3-(1-acrylazacyclobutan-3-yl)imidazo[1,5-a]pyrazin-8-amine

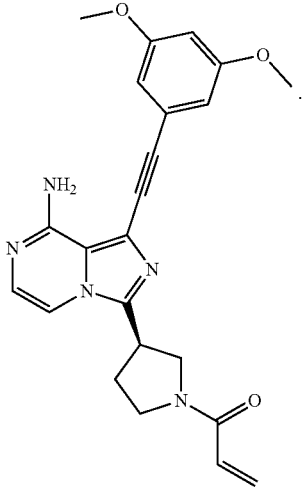

(R)-1-((3,5-Dimethoxyphenyl)ethynyl)-3-(1-acrylpyrrolidin-3-yl)imidazo[1,5-a]pyrazin-8-amine

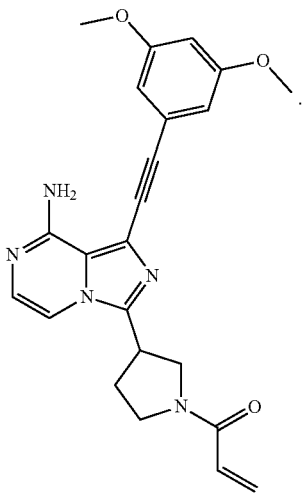

1-((3,5-Dimethoxyphenyl)ethynyl)-3-(1-acrylpyrrolidin-3-yl)imidazo[1,5-a]pyrazin-8-amine

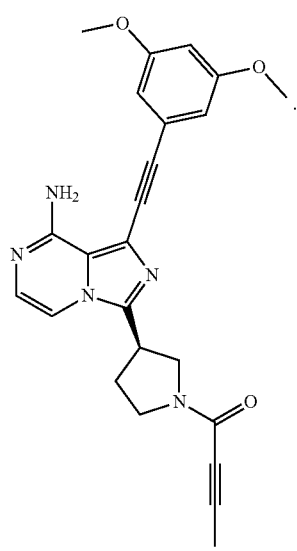
(R)-1-((3,5-dimethoxyphenyl)ethynyl)-3-(1-butan-2-ynoylpyrrolidin-3-yl)imidazo[1,5-a]pyrazin-8-amine
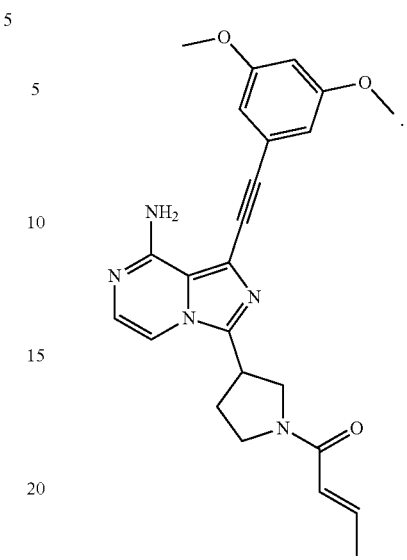
(E)-1-((3,5-Dimethoxyphenyl)ethynyl)-3-(1-butan-2-enoylpyrrolidin-3-yl)imidazo[1,5-a]pyrazin-8-amine
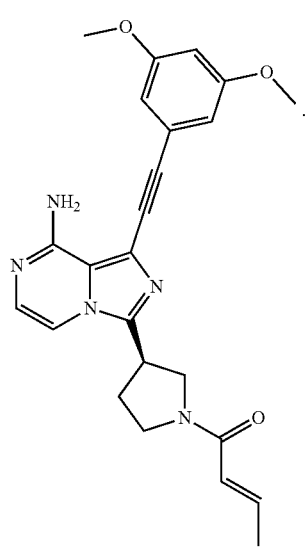
(R)-(E)-1-((3,5-Dimethoxyphenyl)ethynyl)-3-(1-butan-2-enoylpyrrolidin-3-yl)imidazo[1,5-a]pyrazin-8-amine
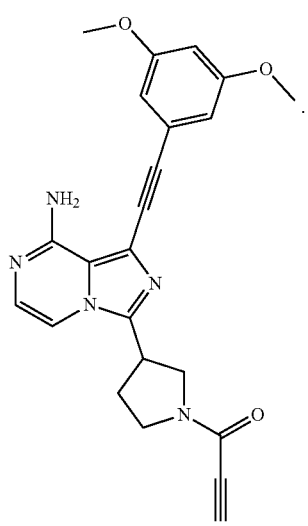
1-((3,5-Dimethoxyphenyl)ethynyl)-3-(1-propynoylpyrrolidin-3-yl)imidazo[1,5-a]pyrazin-8-amine

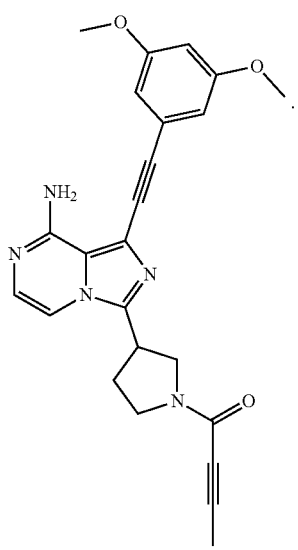

1-((3,5-Dimethoxyphenyl)ethynyl)-3-(1-butan-2-ynoylpyrolidin-3-yl)imidazo[1,5-a]pyrazin-8-amine

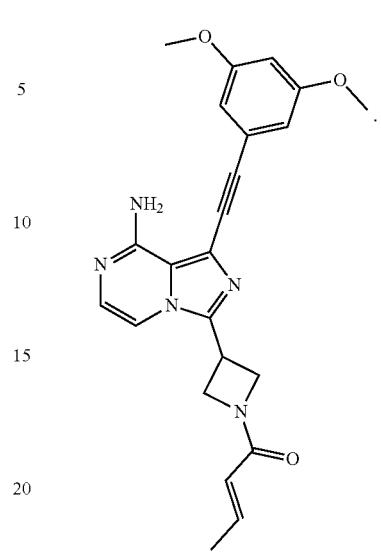

(E)-1-((3,5-Dimethoxyphenyl)ethynyl)-3-(1-but-2-enoylazacyclobutan-3-yl)imidazo[1,5-a]pyrazin-8-amine

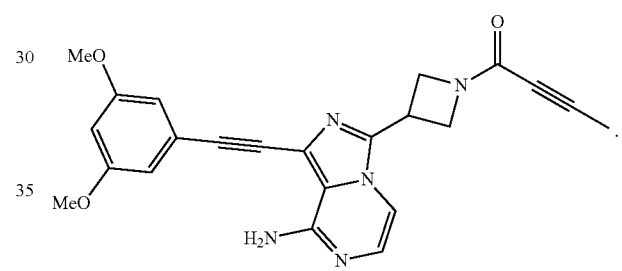

1-((3,5-Dimethoxyphenyl)ethynyl)-3-(1-but-2-ynoylazacyclobutan-3-yl)imidazo[1,5-a]pyrazin-8-amine

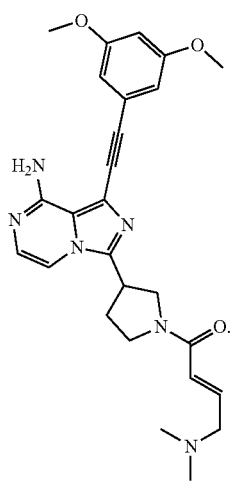

(E)-1-((3,5-Dimethoxyphenyl)ethynyl)-3-(1-(4-dimethylamino))butan-2-enoylpyrrolidin-3-yl)imidazo[1,5-a]pyrazin-8-amine

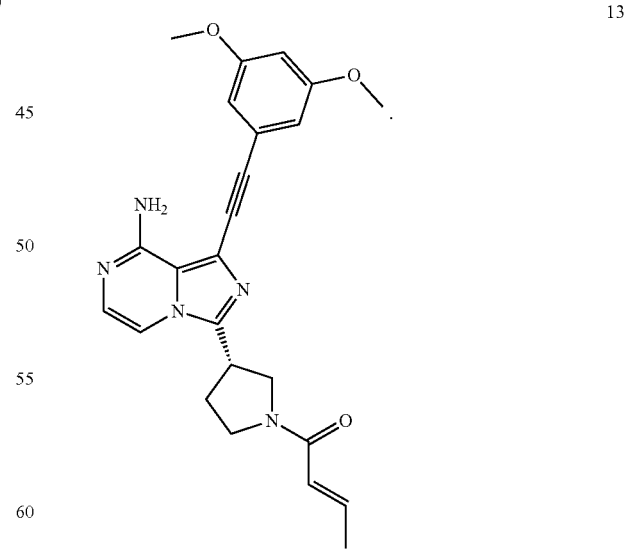

(S)-(E)-1-((3,5-Dimethoxyphenyl)ethynyl)-3-(1-butan-2-enoylpyrrolidin-3-yl)imidazo[1,5-a]pyrazin-8-amine

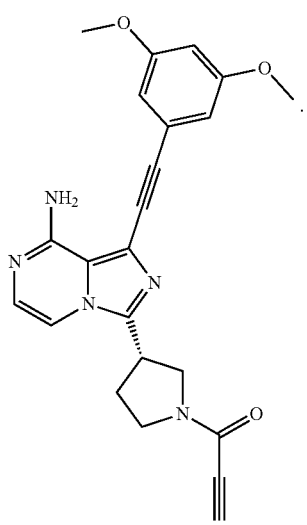
(S)-1-((3,5-Dimethoxyphenyl)ethynyl)-3-(1-propynoylpyrrolidin-3-yl)imidazo[1,5-a]pyrazin-8-amine
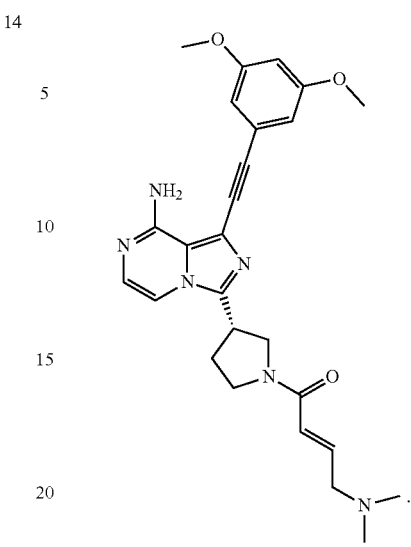
(S)-(E)-1-((3,5-Dimethoxyphenyl)ethynyl)-3-(1-(4-dimethylamino))butan-2-enoylpyrrolidin-3-yl)imidazo[1,5-a]pyrazin-8-amine
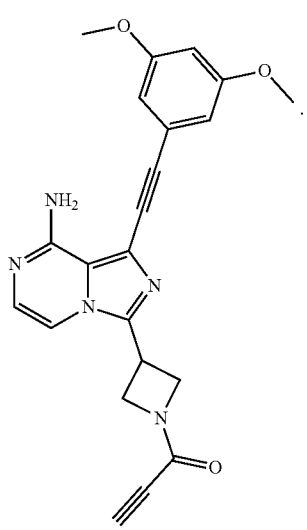
1-((3,5-Dimethoxyphenyl)ethynyl)-3-(1-propynoylazacyclobutan-3-yl)imidazo[1,5-a]pyrazin-8-amine
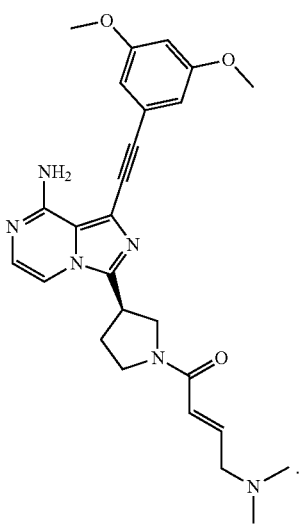
(R)-(E)-1-((3,5-Dimethoxyphenyl)ethynyl)-3-(1-(4-dimethylamino))butan-2-enoylpyrrolidin-3-yl)imidazo[1,5-a]pyrazin-8-amine

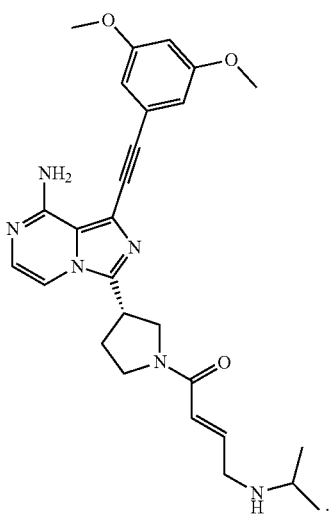

(S)-(E)-1-((3,5-Dimethoxyphenyl)ethynyl)-3-(1-(4-isopropylamino))butan-2-enoylpyrrolidin-3-yl)imidazo[1,5-a]pyrazin-8-amine

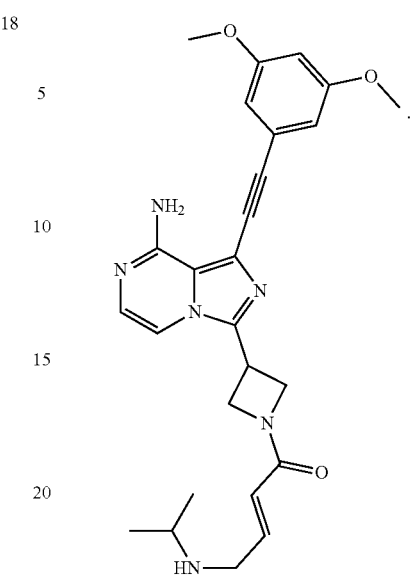

(E)-1-((3,5-Dimethoxyphenyl)ethynyl)-3-(1-(4-isopropylamino))butyl-2-enoylazacyclobutan-3-yl)imidazo[1,5-a]pyrazin-8-amine

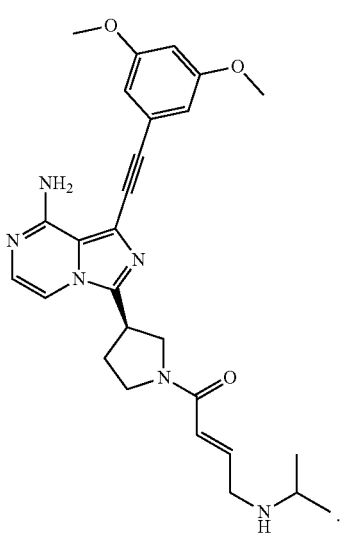

(R)-(E)-1-((3,5-Dimethoxyphenyl)ethynyl)-3-(1-(4-isopropylamino))butan-2-enoylpyrrolidin-3-yl)imidazo[1,5-a]pyrazin-8-amine or tautomers, mesomers, racemates, enantiomers, diastereoisomers thereof, mixtures thereof and pharmaceutically acceptable salts thereof.

The compound according to the present invention is an effective inhibitor of FGFR, Therefore, the compound according to the present invention can be used to treat or prevent FGFR-mediated diseases, including but not limited to tumors and inflammatory diseases, such as osteoarthritis. The compound according the present invention can be used to treat or prevent FGFR-related cancers, such as rhabdomyosarcoma, renal cell carcinoma, multiple myeloma, breast cancer, ovarian cancer, endometrial cancer, cervical cancer, gastric cancer, colon cancer, bladder cancer, pancreatic cancer, lung cancer, breast cancer, prostate cancer and liver cancer (such as hepatocellular carcinoma), more specifically hepatocellular cancer and bladder cancer.

The present invention further relates to a pharmaceutical composition comprising a compound of the invention or its isomers, prodrugs, stable isotope derivatives or pharmaceutically acceptable salts, and pharmaceutically acceptable carriers, diluents and excipients.

Another aspect of the invention relates to a use of compounds shown in general formula (I) or their isomers, prodrugs, stable isotope derivatives or pharmaceutically acceptable salts, or pharmaceutical compositions in the preparation of medicines for the treatment or prevention of diseases mediated by FGFR, such as tumors. Another aspect of the present invention relates to a use of a compound as shown in general formula (I) or a tautomer, a mesomer, a racemate, an enantiomer, a diastereoisomer thereof, a mixture thereof, and a pharmaceutically acceptable salt thereof, or the pharmaceutical composition, in the preparation of a drug for treating and/or preventing diseases such as tumors and inflammatory diseases.

According to the present invention, the drug may be in any pharmaceutical formulation, including but not limited to tablets, capsules, liquids, lyophilized formulations and injections.

The pharmaceutical formulation according to the present invention may be dosed in the form of a dose unit containing a predetermined amount of active ingredients per dose unit. Such a unit dose may comprise, for example, 0.5 mg to 1 g, preferably 1 mg to 700 mg, and particularly preferably 5 mg to 300 mg of the compound according to the present invention, depending on the disease being treated, the method of dosage and the age, weight and condition of the patient, or the pharmaceutical formulation may be dosed in the form of a dose unit containing a predetermined amount of active ingredients per dose unit. A preferred dose unit formulation is that comprising the daily dose or divided dose or a corresponding fraction of the active ingredients as indicated above. In addition, the pharmaceutical formulation can be prepared by a method well known in the pharmaceutical art.

The pharmaceutical formulation according to the present invention can be administrated through any suitable method as required, such as oral (including oral or sublingual), rectal, nasal, topical (including oral, sublingual or transdermal), and vaginal or parenteral (including subcutaneous, intramuscular, intravenous or intradermal) methods. All methods known in the pharmaceutical art can be used to prepare such a formulation by, for example, combining the active ingredients with one or more excipients or one or more adjuvants.

The present invention also relates to a method for treating or preventing FGFR-mediated diseases (e.g. tumors), including administering to patients in need thereof effective doses of the compounds or their isomers, prodrugs, stable isotope derivatives or pharmaceutically acceptable salts, or pharmaceutical compositions of the invention.

A further aspect of the present invention relates to a compound as shown in general formula (I) or an isomer, a prodrug, a stable isotopic derivative thereof or a pharmaceutically acceptable salt, and a pharmaceutical composition containing same and a pharmaceutically acceptable carrier, diluent and excipient thereof, for use in treating or preventing FGFR-mediated diseases, for example, tumors or inflammatory diseases.

Another aspect of the present invention relates to a compound as shown in general formula (I) or a tautomer, a mesomer, a racemate, an enantiomer, a diastereoisomer thereof, a mixture thereof, and a pharmaceutically acceptable salt thereof, for treating and/or preventing diseases such as tumors.

Preparation Schemes

The present invention further provides a method for preparing the compounds.

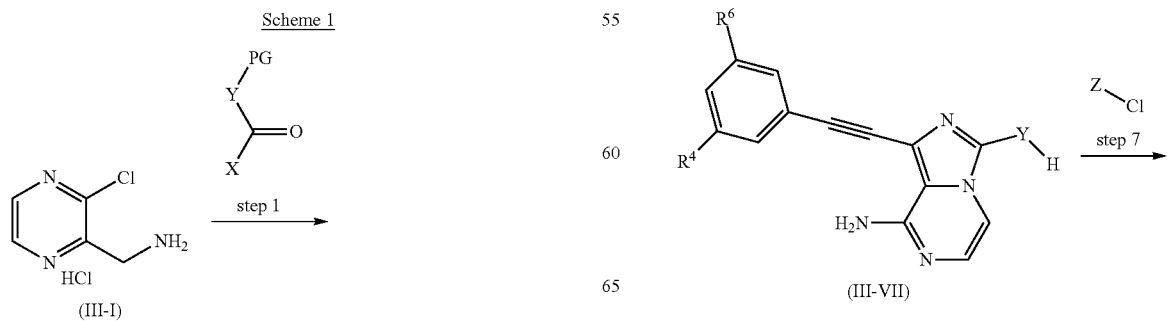

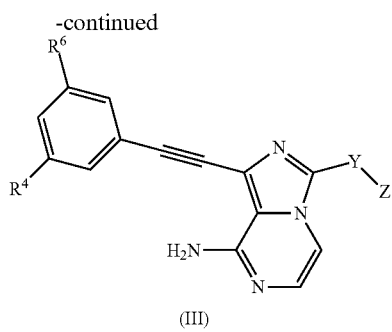

(III)

Step 1:

Y is a 4-5 membered heterocycle containing N atom. PG is the protecting group on the nitrogen atom in ring Y, such as benzyl oxy acyl group. Y and PG are unchanged during the reaction. When X is hydroxyl, the reaction is carried out in methylene chloride, and N,N-diisopropylethylamine is added as the base. The condensation agent used is 2-(1H-benzotriazole-1-yl)-1,1,3,3-tetramethyluronium tetrafluoroborate. The reaction takes place at room temperature. When X is Cl, the reaction is carried out in dichlormethane with the addition of triethyl amine to give compound (III-II);

Step 2:

Y and PG are unchanged during the reaction. When Y is azetidinyl, the reaction is carried out at room temperature in acetonitrile with the addition of condensation agent $POCl_3$ and pyridine as the base; when Y is pyrrolidinyl, the reaction is carried out under heating in acetonitrile with the addition of $POCl_3$ and a catalytic amount of N,N-dimethyl formamide to give compound (III-III);

Step 3:

Y and PG are unchanged during the reaction. N-bromosuccinimide (NBS) is used as the bromination reagent in the bromination reaction, and the reaction is carried out in N,N-dimethyl formamide at room temperature to give compound (III-IV);

Step 4:

Y and PG are unchanged during the reaction. 30% aqueous ammonia solution is employed as nucleophile in the nucleophilic reaction, isopropanol is used as the solvent, and the reaction is heated in a sealed tube to give compound (III-V).

Step 5:

Y and PG are unchanged during the reaction. 3,5-disubstituted phenylacetylene is required in the cross coupling reaction, bases such as triethylamine are used, N,N-dimethyl formamide is used as the reaction solvent, and catalytic amount of cuprous iodide and 1,1'-bis(diphenylphosphino)ferrocene-palladium(II) dichloride are used as the catalysts, the reaction is heated to give compound (III-VI).

Step 6:

Y is unchanged during the reaction. High concentration hydrochloric acid is employed as the de-protection reagent, the reaction is carried out at room temperature, protection group is removed to give compound (III-VII).

Step 7:

Y & Z are unchanged during the reaction. Using related acyl chloride or chloride, base such as triethylamine is added, the reaction is carried out in THF and N,N-dimethyl formamide at room temperature to give compound (III).

MODES OF CARRYING OUT THE INVENTION

Detailed Descriptions

Unless stated to the contrary, the following terms used in the description and the claims have the following meanings.

The expression "Cx-Cy" as used herein represents the range of the number of carbon atoms, where both x and y are integers. For example, C3-C8 cyclyl represents a cyclyl group having 3 to 8 carbon atoms, and —C0-C2 alkyl represents an alkyl group having 0 to 2 carbon atoms, where —C0 alkyl refers to a single chemical bond.

The term "alkyl" as used herein refers to a saturated aliphatic hydrocarbon group, including linear and branched groups having 1 to 20 carbon atoms, for example, linear and branched groups having 1 to 18 carbon atoms, 1 to 12 carbon atoms, 1 to 8 carbon atoms, 1 to 6 carbon atoms or 1 to 4 carbon atoms. Non-limiting examples include methyl, ethyl, n-propyl, i-propyl, n-butyl, i-butyl, t-butyl, s-butyl, n-pentyl, 1,1-dimethyl propyl, 1,2-dimethyl propyl, 2,2-dimethyl propyl, 1-ethyl propyl, 2-methyl butyl, 3-methyl butyl, n-hexyl, 1-ethyl-2-methyl propyl, 1,1,2-trimethyl propyl, 1,1-dimethyl butyl, 1,2-dimethyl butyl, 2,2-dimethyl butyl, 1,3-dimethyl butyl, 2-ethyl butyl, and various branched isomers thereof, etc. Alkyl may be substituted or unsubstituted.

The term "cyclyl" or "cyclic group" used herein refers to saturated or partially unsaturated monocyclic or polycyclic hydrocarbon groups, comprising 3 to 12 cyclic carbon atoms, such as 3 to 12, 3 to 10, 3 to 8 or 3 to 6 cyclic carbon atoms, or 3, 4, 5, 6-membered rings. Non-limiting examples of monocyclic cyclyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Cyclyl may be substituted or unsubstituted.

The term "heterocyclyl" used herein refers to a saturated or partially unsaturated monocyclic or polycyclic hydrocarbon group, comprising 3 to 20 ring atoms, such as 3 to 16, 3 to 12, 3 to 10, 3 to 8 or 3 to 6 ring atoms, where one or more ring atoms are heteroatoms selected from the group consisting of nitrogen, oxygen or $S(O)_m$ (where m is an integer of 0 to 2), but excluding ring parts of —O—O—, —O—S— or —S—S—, and the remaining ring atoms are carbon. Preferably 3 to 12 ring atoms, of which 1 to 4 are heteroatoms, are comprised. More preferably the heterocyclyl ring comprises 3 to 10 ring atoms, more preferably 3 to 8 ring atoms. Most preferred are 5-membered rings or 6-membered rings, where 1 to 4 members are heteroatoms, more preferably 1 to 3 are heteroatoms, and most preferably 1 to 2 are heteroatoms. Non-limiting examples of monocyclic heterocyclyl include pyrrolidinyl, piperidyl, piperazinyl, morpholinyl, thiomorpholinyl, homopiperazinyl and the like. Polycyclic heterocyclic groups include spirocyclic, fused and bridged cyclic heterocyclyl groups.

The term "spiroheterocyclic group" used herein refers to a 5 to 20 membered polycyclic heterocyclic group with one atom (referred to as a spiro atom) shared between monocyclic rings, where one or more of the ring atoms are heteroatoms selected from the group consisting of nitrogen, oxygen or $S(O)_m$ (where m is an integer of 0 to 2), and the rest of the ring atoms are carbon. They may contain one or more double bonds, but none of the rings has a completely conjugated pi electron system. They are preferably 6 to 14 membered, and more preferably 7 to 10 membered. According to the number of spiro atoms shared between rings, spirocyclyl groups are divided into mono-spiroheterocyclyl, bi-spiroheterocyclyl or poly-spiroheterocyclyl, preferably mono-spirocyclyl and bi-spirocyclyl, and more preferably 4 membered/4 membered, 4 membered/5 membered, 4 membered/6 membered, 5 membered/5 membered, or 5 membered/6 membered mono-spirocyclyl. Non-limiting examples of spirocyclyl include

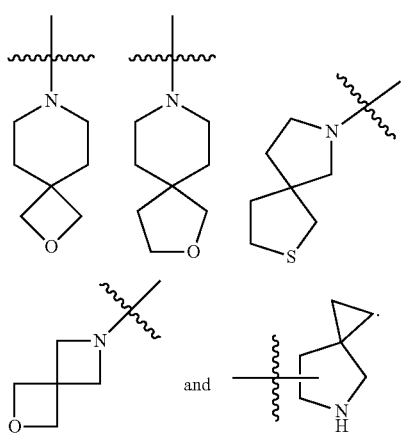

The term "fused heterocyclyl" used herein refers to a 5 to 20 membered polycyclic heterocyclyl group where each ring in the system shares a pair of adjacent atoms with other rings in the system, one or more rings may contain one or more double bonds, but none of the rings has a completely conjugated pi electron system, where one or more ring atoms are heteroatoms selected from the group consisting of nitrogen, oxygen or S(O)$_m$ (where m is an integer of 0 to 2), and the remaining ring atoms are carbon. They are preferably 6 to 14 membered, and more preferably 7 to 10 membered. According to the number of rings, they can be divided into bicyclic, tricyclic, tetracyclic or polycyclic fused heterocyclyl, and the fused heterocyclyl groups are preferably bicyclic or tricyclic, and more preferably 5 membered/5 membered, or 5 membered/6 membered bicyclic fused heterocyclyl. Non-limiting examples of fused heterocyclyl include

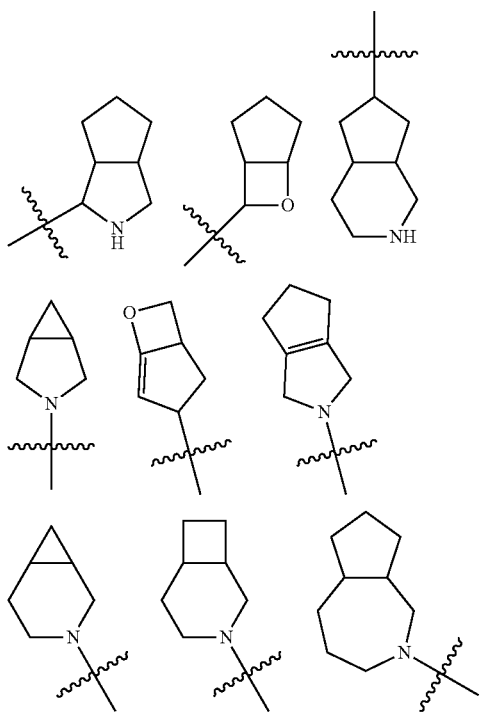

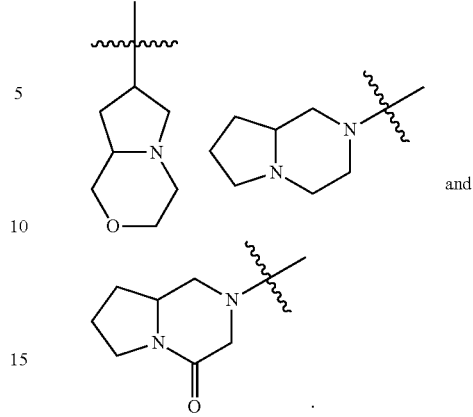

The heterocyclyl ring may be fused to an aryl, a heteroaryl or a cyclyl ring, in which the ring connected with the parent structure is a heterocyclyl group, and the non-limiting examples include:

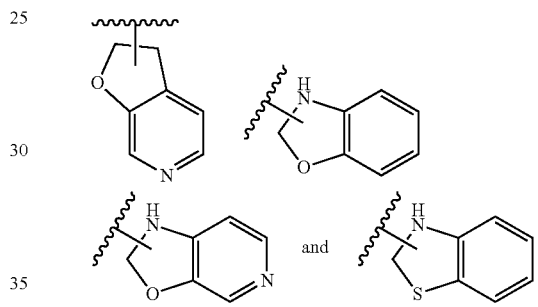

and the like.

The heterocyclyl group may be substituted or unsubstituted.

The term "aryl" used herein refers to a 6 to 14 membered all-carbon monocyclic or condensed polycyclic (i.e., rings sharing adjacent pairs of carbon atoms) group, and a polycyclic (i.e., rings bearing adjacent pairs of carbon atoms) group having a conjugated pi-electron system, preferably 6 to 10 membered, for example, phenyl and naphthyl, and most preferably phenyl. The aryl ring may be fused to a heteroaryl, a heterocyclyl or a cyclyl ring, in which the ring connected with the parent structure is an aryl ring, and the non-limiting examples include:

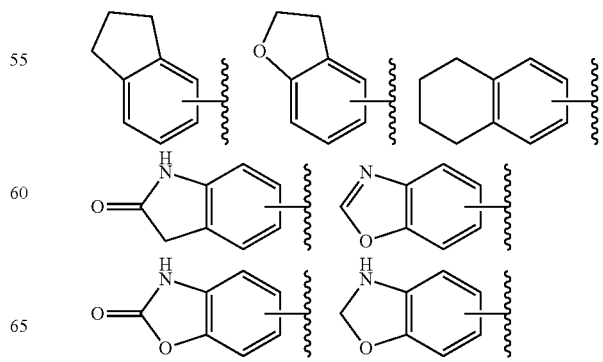

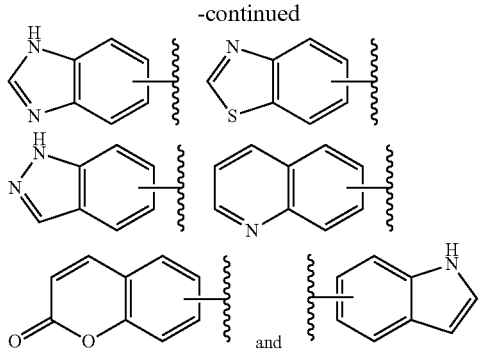

Aryl may be substituted or unsubstituted.

The term "heteroaryl" herein refers to a heteroaromatic system comprising 1 to 4 heteroatoms and 5 to 14 ring atoms, where the heteroatoms include oxygen, sulfur and nitrogen. Heteroaryl is preferably 5 to 10 membered, and more preferably 5 membered or 6 membered, e.g., furyl, thienyl, pyridyl, pyrrolyl, N-alkylpyrrolyl, pyrimidinyl, pyrazinyl, imidazolyl, tetrazyl, oxazolyl, and isoxazolyl etc. The heteroaryl ring can be fused to an aryl, a heterocyclyl or a cyclyl ring, where the ring connected with the parent structure is a heteroaryl ring, and the non-limiting examples include:

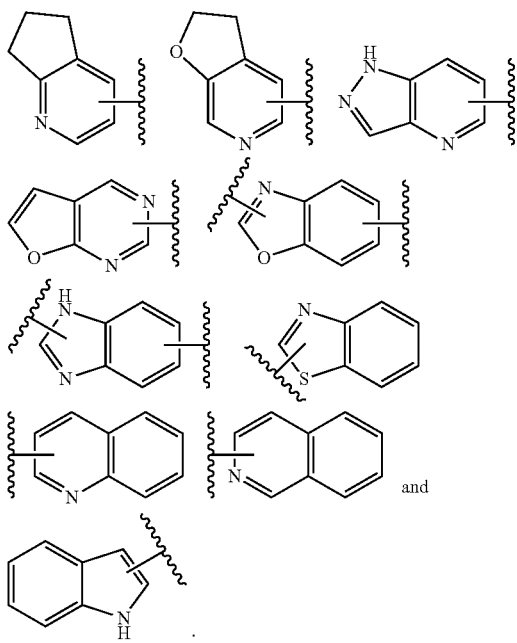

Heteroaryl may be substituted or unsubstituted.

The term "halogen" herein refers to fluorine, chlorine, bromine or iodine.

The term "cyano" herein refers to —CN.

The term "alkenyl" herein refers to a linear, branched hydrocarbon group containing at least one carbon-carbon double bond, including linear and branched groups having 2 to 20 carbon atoms, for example, linear and branched groups having 2 to 18 carbon atoms, 2 to 12 carbon atoms, 2 to 8 carbon atoms, 2 to 6 carbon atoms or 2 to 4 carbon atoms. Where 1 to 3 carbon-carbon double bonds may be present and preferably 1 carbon-carbon double bond may be present.

The term "C2-4 alkenyl" refers to alkenyl having 2 to 4 carbon atoms, including vinyl, propenyl, butenyl, buten-2-yl. The alkenyl group may optionally be substituted.

The term "alkynyl" herein refers to a linear, or branched hydrocarbon group containing at least one carbon-carbon triple bond, including linear and branched groups having 2 to 20 carbon atoms, for example, linear and branched groups having 2 to 18 carbon atoms, 2 to 12 carbon atoms, 2 to 8 carbon atoms, 2 to 6 carbon atoms or 2 to 4 carbon atoms. Among them, 1 to 3 carbon-carbon triple bonds may be present and preferably 1 carbon-carbon triple bond may be present. The term "C2-4 alkynyl" refers to alkynyl having 2 to 4 carbon atoms, Non-limiting examples including acetenyl, propynyl, butynyl and butyn-2-yl.

The term "heteroalkyl" herein refers to a stable straight-chain or branched-chain hydrocarbon group consisting of a specified number of carbon atoms and at least one heteroatom selected from oxygen, nitrogen and sulfur. Among them, nitrogen and sulfur atoms may be oxidized optionally, nitrogen atoms may be quaternized optionally, and hetero atoms such as oxygen, nitrogen and sulfur may be located at any internal position of the heteroalkyl group, or at the position where the alkyl group is connected with the rest of the molecule. More than two heteroatoms may be independent or continuous.

The term "alkyloxy" herein refers the alkyl group connected by an oxygen bridge, comprising alkyloxy group, cyclyloxy and heterocyclyloxy group. Thus, the alkyl in the term "alkoxy" includes alkyl, heterocyclyl and cyclyl or cyclic group as defined above.

The "optional" and "optionally" used herein means that an event or environment described subsequently may but does not necessarily occur, including cases where the event or environment occurs or does not occur. For example, "heterocyclyl optionally substituted by alkyl" means that alkyl may but does not necessarily exist, including cases where heterocyclyl is substituted by alkyl and not substituted by alkyl.

The term "substituted" used herein refers that one or more hydrogen atoms, preferably at most 5 and more preferably 1 to 3 hydrogen atoms, in a group are substituted independently with a corresponding number of substituents. It goes without saying that, substituents are only located in their possible chemical positions, and a person skilled in the art can determine (experimentally or theoretically) possible or impossible substitutions without a lot of efforts. For example, amino or hydroxy groups having free hydrogen may be unstable when combined with carbon atoms having unsaturated (e.g. olefinic) bonds.

The term "substituent(s)" include, but are not limited to, the alkyl, alkenyl, alkynyl, alkoxy, halogen, hydroxyl, amino, cyano and thiol groups.

The term "pharmaceutical composition" herein represents a mixture of one or more of the compounds described herein or physiologically/pharmaceutically acceptable salts or prodrugs with other chemical components, as well as other components such as physiologically/pharmaceutically acceptable carriers and excipients. An object of the pharmaceutical compositions is to promote the dosage of drugs to organisms, facilitate the absorption of active ingredients and thus exert biological activity.

The term "room temperature" in the present invention refers to 15 to 30° C.

The term "a stable isotopic derivative" used herein includes: derivatives substituted with isotopes, such as derivatives obtained by substituting any hydrogen atom in Formula I with 1 to 5 deuterium atoms, derivatives substituted with isotopes obtained by substituting any carbon atom in Formula I with 1 to 3 carbon-14 atoms, or derivatives substituted with isotopes obtained by substituting any oxygen atom in Formula I with 1 to 3 oxygen-18 atoms.

The "pharmaceutically acceptable salts" as described in the present invention are discussed in Berge, et al., "Pharmaceutically acceptable salts," *J. Pharm. Sci.*, 66, 1-19 (1977), and it is obvious to pharmaceutical chemists that said salts are essentially non-toxic and can provide desired pharmacokinetic properties, palatability, absorption, distribution, metabolism or excretion, and the like.

The "pharmaceutically acceptable salts" according to the present invention can be synthesized through a common chemical method.

In general, the preparation of the salts can be achieved by reacting the compounds in the form of free alkalis or acids with equivalent chemical equivalents or excess amounts of acids (inorganic or organic acids) or alkalis in suitable solvents or solvent compositions.

The "prodrug" as described in the present invention refers to a compound that can be converted into an original active compound after being metabolized in vivo. Representatively speaking, prodrugs are inactive substances, or have activity lower than the active parent compounds but can provide convenient operation and dosage or improve metabolic characteristics.

The "isomer" of the present invention refers that the compound of Formula (I) according to the present invention may have one or more asymmetric center and may be a racemate, a racemic mixture and a single diastereoisomer. The isomers such as enantiomers, diastereoisomers, stereoisomers, geometric isomers and conformational isomers, are all included in the present invention. The geometric isomers include cis- and trans-isomers.

The term "tumor" herein includes benign tumor and malignant tumor, for example, cancer.

The term "cancer" herein includes various malignant tumors in which FGFR is involved, including but not limited to liver cancer (especially hepatocellular carcinoma), bladder cancer, lung cancer, breast cancer, prostate cancer, rhabdomyosarcoma, renal cell cancer, myeloma, gastric cancer, pancreatic cancer and colon cancer.

The term "inflammatory disease" herein refers to any inflammatory disease in which FGFR is involved.

The term "a therapeutically effective amount/dose" herein refers to the amount of the compound according to the present invention that could effectively inhibits FGFR and/or treats the diseases.

EXAMPLES

The present invention will be further illustrated by means of examples below, but is not therefore limited to the scope of the examples described. In the following examples, experimental methods without specific conditions noted are selected according to conventional methods and conditions or according to product instructions.

The structures of all the compounds according to the present invention can be identified by nuclear magnetic resonance (1H NMR) and/or mass spectrometric detection (MS).

$^1$H NMR chemical shift ($\delta$) is recorded in PPM (unit: $10^{-6}$ PPM). NMR is carried out by a Bruker AVANCE-400 spectrometer. Appropriate solvents include deuterated chloroform ($CDCl_3$), deuterated methanol ($CD_3OD$) and deuterated dimethylsulfoxide (DMSO-$d^6$), with tetramethylsilane as an internal standard (TMS).

The low resolution mass spectrogram (MS) is determined by an Agilent 1260 HPLC/6120 mass spectrometer, using Agilent ZORBAX XDB-C18, 4.6×50 mm, 3.5 μm, at a gradient elution condition I: 0: 95% solvent A1 and 5% solvent B1, 1-2:5% solvent A1 and 95% solvent B1; 2.01-2.50: 95% solvent A1 and 5% solvent B1. The percentage is the volume percentage of a certain solvent based on the total solvent volume. Solvent A1: 0.01% formic acid aqueous solution; solvent B1: 0.01% formic acid solution in acetonitrile; and the percentage is the volume percentage of a solute based on the solution.

The thin-layer silica gel plate is a Yantai Yellow Sea HSGF254 or Qingdao GF254 silica gel plate. The Yantai Yellow Sea 100-200 or 200-300 mesh silica gel is generally used as the support in the column chromatography.

The known starting raw materials of the present invention can be synthesized by or in accordance with methods known in the art, or can be purchased from companies such as Acros Organics, Aldrich Chemical Company, Accela ChemBio Inc., Shanghai Bide Pharmatech, Shanghai Aladdin Chemistry, Shanghai Meryer Chemistry, Accelerating Chemistry, etc.

In the examples, unless stated specially, the solvents used in the reaction are all anhydrous solvents, where anhydrous tetrahydrofuran is commercially available tetrahydrofuran, sodium blocks are used as a dehydrant, benzophenone is used as an indicator, the solution is refluxed under the protection of nitrogen gas until the it assumes a bluish violet color, it is distilled and collected, and stored at room temperature under the protection of nitrogen gas, and the other anhydrous solvents are purchased from Aladdin Chemistry and Accelerating Chemistry, and transfer and use of all anhydrous solvents shall be carried out under the protection of nitrogen gas unless specially noted.

In the examples, the reactions are all carried out under an argon atmosphere or nitrogen atmosphere unless specially noted.

The argon atmosphere or nitrogen atmosphere refers that the reaction flask is connected to an argon or nitrogen balloon with a volume of about 1 L.

The hydrogen atmosphere refers that the reaction flask is connected to a hydrogen balloon with a volume of about 1 L.

In hydrogenation, the reaction is usually vacuumed and filled with hydrogen gas, and this is repeated 3 times.

The reaction temperature is the room temperature, and the temperature range is from 15° C. to 30° C., unless specially noted.

The thin-layer chromatography method (TLC) is employed to monitor the reaction process in the examples. The developer system used in the reaction includes: A, which is a dichloromethane and methanol system, and B: which is a petroleum ether and ethyl acetate system, and the ratio by volume of the solvents is adjusted according to the polarity of the compounds.

The eluent system for column chromatography and the developer system for thin-layer chromatography employed in the purification of compounds include: A, which is a dichloromethane and methanol system, and B: which is a petroleum ether and ethyl acetate system, and the ratio by volume of the solvents is adjusted according to the polarity of the compounds, and a small amount of triethyl amine and acid or alkaline reagents and the like can also be added for the adjustment.

Example 1

(S)-1-((3,5-Dimethoxyphenyl)ethynyl)-3-(1-acryl pyrrolidin-3-yl)imidazo[1,5-a]pyrazin-8-amine

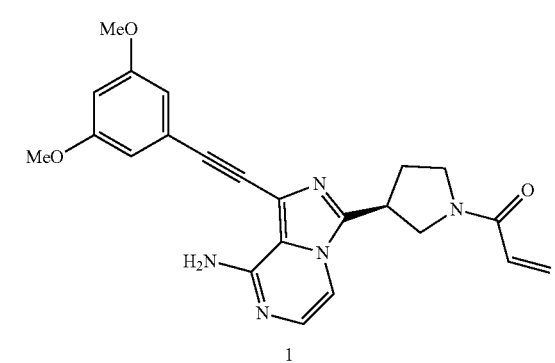

1

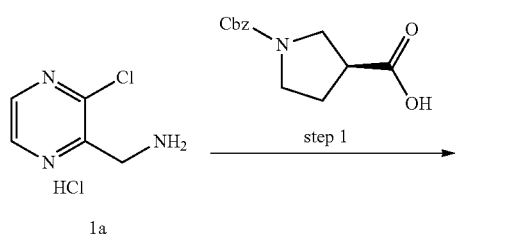

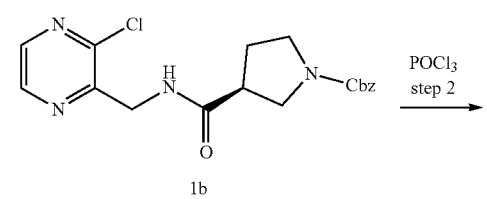

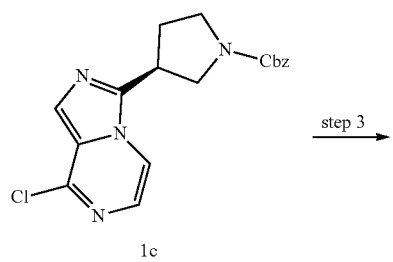

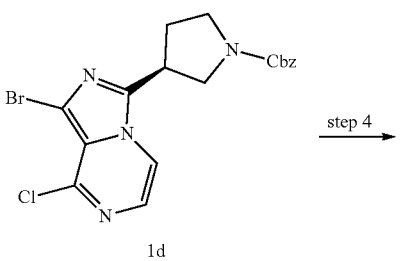

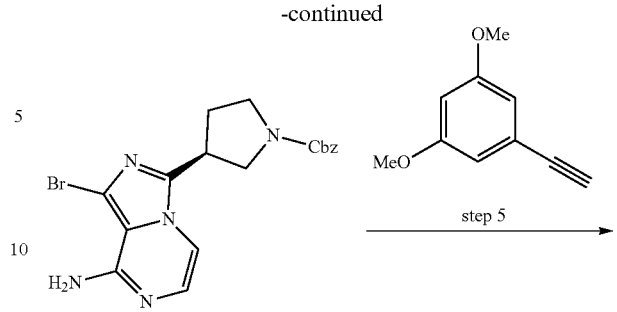

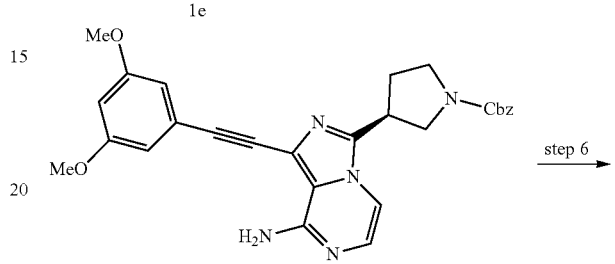

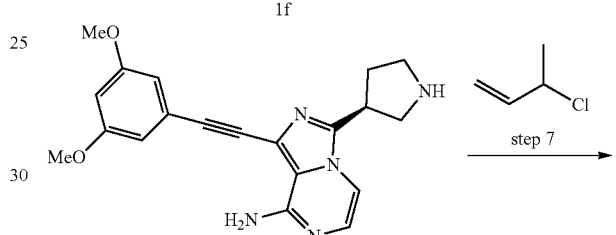

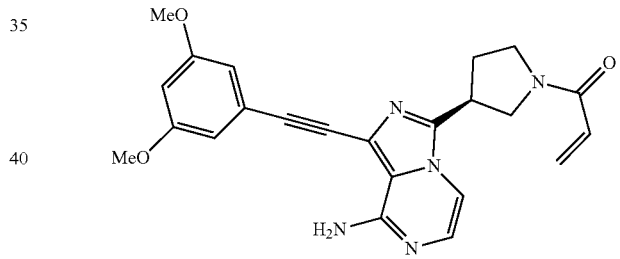

Step 1

Benzyl-(S)-3-(((3-chloropyrazin-2-yl)methyl)carbamoyl) pyrrolidine-1-carboxylate To a solution of (3-chloropyrazin-2-yl)methanamine hydrochloride 1a (3.1 g, 21.7 mmol), 2-(1H-benzotriazole-1-yl)-1,1,3,3-tetramethyluronium tetrafluoroborate (7.1 g, 22 mmol) and N,N-diisopropylethylamine (9.3 g, 72 mmol) in dichloromethane (100 mL) at room temperature, (S)-1-((benzyloxy)carbonyl)pyrrolidine-3-carboxylic acid (4.5 g, 18 mmol) was added in several batches. The resulting mixture was stirred at room temperature for 16 h. The reaction was quenched with water (30 mL) and the organic phase was separated. The aqueous phase was extracted with dichloromethane (50 mL×2), the combined organic phase was washed with saturated brine (50 mL×2), dried over anhydrous sodium sulfate and filtered. The filtrate was concentrated under vacuum and the residue was purified by flash column chromatography (dichloromethane/methanol 20:1) to provide benzyl-(S)-3-(((3-chloropyrazin-2-yl) methyl)carbamoyl) pyrrolidine-1-carboxylate 1b (4.85 g, 13.0 mmol, yellow oil). Yield: 72%.

$^1$H NMR (400 MHz, CDCl$_3$) δ8.43 (d, J=2.4 Hz, 1H), 8.34 (d, J=2.4 Hz, 1H), 7.37-7.26 (m, 5H), 6.92-6.85 (bs, 1H), 5.14 (s, 2H), 4.71 (d, J=4.4 Hz, 2H), 3.88-3.51 (m, 3H), 3.22-3.05 (m, 2H), 2.31-2.07 (m, 2H).

Step 2

Benzyl-(S)-3-(8-chloroimidazo[1,5-a]pyrazin-3-yl) pyrrolidine-1-carboxylate

To a solution of benzyl-(S)-3-(((3-chloropyrazin-2-yl) methyl)carbamoyl) pyrrolidine-1-carboxylate 1 b (4.85 g, 11.8 mmol) in acetonitrile (60 mL) at room temperature, were added dropwise phosphorus oxychloride (9.2 g, 60 mmol) and N,N-dimethylformamide (0.1 mL). Under nitrogen, the resulting mixture was heated to 80° C. and stirred for 2 h. The mixture was cooled to room temperature and concentrated under vacuum to remove solvent. The residue was neutralized by adding saturated sodium bicarbonate solution. The mixture was extracted with dichloromethane (80 mL×3) and the combined organic phase was washed with saturated brine (50 mL×2), dried over anhydrous sodium sulfate and filtered. The filtrate was concentrated under vacuum and the residue was purified by flash column chromatography (2:1-1:2 hexane/ethyl acetate) to provide benzyl-(S)-3-(8-chloroimidazo[1,5-a]pyrazin-3-yl)pyrrolidine-1-carboxylate 1c (1.41 g, 3.9 mmol, yellow oil). Yield: 33%.

$^1$H NMR (400 MHz, CDCl$_3$) δ7.81 (s, 1H), 7.62 (d, J=4.8 Hz, 1H), 7.42-7.26 (m, 6H), 5.16 (s, 2H), 4.10-3.95 (m, 1H), 3.88-3.65 (m, 3H), 3.64-3.55 (m, 1H), 2.66-2.32 (m, 2H).

Step 3

Benzyl-(S)-3-(1-bromo-8-chloroimidazo[1,5-a] pyrazin-3-yl)pyrrolidine-1-carboxylate A suspension of benzyl-(S)-3-(8-chloroimidazo[1,5-a]pyrazin-3-yl)pyrrolidine-1-carboxylate 1c (1.42 g, 4.0 mmol), N-bromosuccinimide (0.71 g, 4.0 mmol) in N,N-dimethylformamide (15 mL) was stirred at room temperature for 1 h. The reaction was quenched with saturated aqueous sodium thiosulfate solution and extracted with dichloromethane (50 mL×3). The combined organic phase was washed with saturated brine (50 mL×2), dried over anhydrous sodium sulfate and filtered: The filtrate was concentrated under vacuum and the residue was purified by flash column chromatography (2:1-1:2 hexane/ethyl acetate) to provide benzyl-(S)-3-(1-bromo-8-chloroimidazo[1,5-a] pyrazin-3-yl)pyrrolidine-1-carboxylate 1d (1.45 g, 3.3 mmol, yellow oil). Yield: 86%.

$^1$H NMR (400 MHz, CDCl$_3$) δ7.60 (d, J=4.8 Hz, 1H), 7.44-7.26 (m, 6H), 5.15 (s, 2H), 4.01-3.85 (m, 1H), 3.84-3.61 (m, 3H), 3.60-3.52 (m, 1H), 2.63-2.28 (m, 2H).

Step 4

Benzyl-(S)-3-(8-amino-1-bromoimidazo[1,5-a] pyrazin-3-yl)pyrrolidine-1-carboxylate In a sealed tube (120 mL) benzyl-(S)-3-(1-bromo-8-chloroimidazo[1,5-a]pyrazin-3-yl)pyrrolidine-1-carboxylate 1d (1.45 g, 3.3 mmol) and isopropanol (30 mL), ammonium hydroxide (30% aqueous solution, 4 mL) was added dropwise under stirring. The tube was sealed and the mixture was heated to 100° C. for 6 h. Upon cooled to room temperature, the reaction mixture was diluted with water (30 mL) and extracted with ethyl acetate (50 mL×3). The organic phase was washed with saturated brine (50 mL×2). The combined organic phase was dried over anhydrous sodium sulfate and filtered. The residue was purified by silica-gel column chromatography (20:1-10:1 dichloromethane/methanol) to provide benzyl-(S)-3-(8-amino-1-bromoimidazo[1,5-a] pyrazin-3-yl)pyrrolidine-1-carboxylate 1e (1.12 g, 2.7 mmol, yellow oil). Yield: 82%.

$^1$H NMR (400 MHz, CDCl$_3$) δ7.43-7.26 (m, 5H), 7.17 (d, J=4.8 Hz, 1H), 7.16 (d, J=4.8 Hz, 1H), 6.02-5.58 (bs, 2H), 5.15 (s, 2H), 4.03-3.88 (m, 1H), 3.84-3.51 (m, 4H), 2.63-2.26 (m, 2H).

Step 5

Benzyl-(S)-3-(8-amino-1-((3,5-dimethoxyphenyl) ethynyl) imidazo[1,5-a]pyrazin-3-yl)pyrrolidine-1-carboxylate To a solution of benzyl-(S)-3-(8-amino-1-bromoimidazo [1,5-a]pyrazin-3-yl)pyrrolidine-1-carboxylate 1e (1.22 g, 2.7 mmol), 1-ethynyl-3,5-dimethoxybenzene (2.46 g, 15.0 mmol) and triethylamine (3.0 g, 30 mmol) in N,N-dimethylformamide (20 mL) under nitrogen, were added cuprous iodide (60 mg, 0.3 mmol) and 1,1'-bis(diphenylphosphino) ferrocene-palladium(II)dichloride (110 mg, 0.15 mmol). The mixture was heated to 80° C. and stirred for 5 h under nitrogen. The mixture was cooled to room temperature, quenched with saturated ammonium chloride solution (10 mL) and extracted with dichloromethane (50 mL×3). The organic phase was washed with saturated brine (20 mL×2). The combined organic phase was dried over anhydrous sodium sulfate and filtered. The residue was purified by silica-gel column chromatography (20:1-10:1 dichloromethane/methanol) to provide Benzyl-(S)-3-(8-amino-1-((3, 5-dimethoxyphenyl)ethynyl) imidazo[1,5-a]pyrazin-3-yl) pyrrolidine-1-carboxylate 1f (310 mg, 0.62 mmol, grey solid), yield: 23%.

$^1$H NMR (400 MHz, CDCl$_3$) δ7.48-7.26 (m, 5H), 7.24-7.04 (m, 2H), 6.71 (s, 2H), 6.50 (s, 1H), 5.97-5.58 (bs, 2H), 5.15 (s, 2H), 4.02-3.88 (m, 1H), 3.80 (s, 6H), 3.83-3.51 (m, 4H), 2.68-2.25 (m, 2H).

Step 6

(S)-1-((3,5-Dimethoxyphenyl)ethynyl)-3-(pyrrolidin-3-yl)imidazo[1,5-a]pyrazin-8-amine hydrochloride salt A suspension of benzyl-(S)-3-(8-amino-1-((3,5-dimethoxyphenyl)ethynyl)imidazo[1,5-a]pyrazin-3-yl) pyrrolidine-1-carboxylate 1f (310 mg, 0.62 mmol, grey solid) in hydrochloric acid (37% aqueous solution, 2 mL) was stirred at room temperature for 48 h. The reaction mixture was diluted with ultrapure water (20 mL) and extracted with diethyl ether (5 mL). The resulting aqueous phase was concentrated under vacuum to provide (S)-1-((3,5-dimethoxyphenyl)ethynyl)-3-(pyrrolidin-3-yl)imidazo[1,5-a]pyrazin-8-amine hydrochloride salt 1g (196 mg, 0.45 mmol, yellow solid). Yield: 73%.

MS m/z (ESI): 364 [M+1].

Step 7

(S)-1-((3,5-Dimethoxyphenyl)ethynyl)-3-(1-acrylpyrrolidin-3-yl)imidazo[1,5-a]pyrazin-8-amine A suspension of (S)-1-((3,5-dimethoxyphenyl)ethynyl)-3-(pyrrolidin-3-yl)imidazo[1,5-a]pyrazin-8-amine hydrochloride salt 1g (196 mg, 0.45 mmol) and triethylamine (200 mg, 2.0 mmol) in anhydrous N,N-dimethylacetamide (1.0 mL) and anhydrous tetrahydrofuran (1.0 mL) was stirred at 0° C. for 10 min under nitrogen protection. A solution of acryloyl chloride (41 mg, 0.45 mmol) in anhydrous tetrahydrofuran (1 mL) was added dropwise with vigorous stirring, after the addition, the mixture was further stirred for 2 min. The mixture was quenched with saturated sodium bicarbonate solution (10 mL) and extracted with dichloromethane (30 mL×3). The combined organic phase was dried over anhydrous sodium sulfate and filtered. The residue was purified by preparative TLC (20:1 dichloromethane/methanol) to provide (S)-1-((3,5-dimethoxyphenyl)ethynyl)-3-(1-acrylpyrrolidin-3-yl)imidazo[1,5-a]pyrazin-8-amine 1 (57.8 mg, 0.14 mmol, yellow solid). Yield: 31%.

MS m/z (ESI): 418 [M+1];

$^1$H NMR (400 MHz, CDCl$_3$) δ7.24-7.12 (m, 2H), 6.71 (d, J=2.0 Hz, 2H), 6.51-6.49 (m, 1H), 6.48-6.40 (m, 2H), 5.90-5.75 (bs, 2H), 5.74-5.68 (m, 1H), 4.21-4.05 (m, 2H), 4.02-3.91 (m, 1H), 3.81 (s, 6H), 3.80-3.61 (m, 2H), 2.55-2.19 (m, 2H).

Example 2

1-((3,5-Dimethoxyphenyl)ethynyl)-3-(1-acrylazacyclobutan-3-yl)imidazo[1,5-a]pyrazin-8-amine

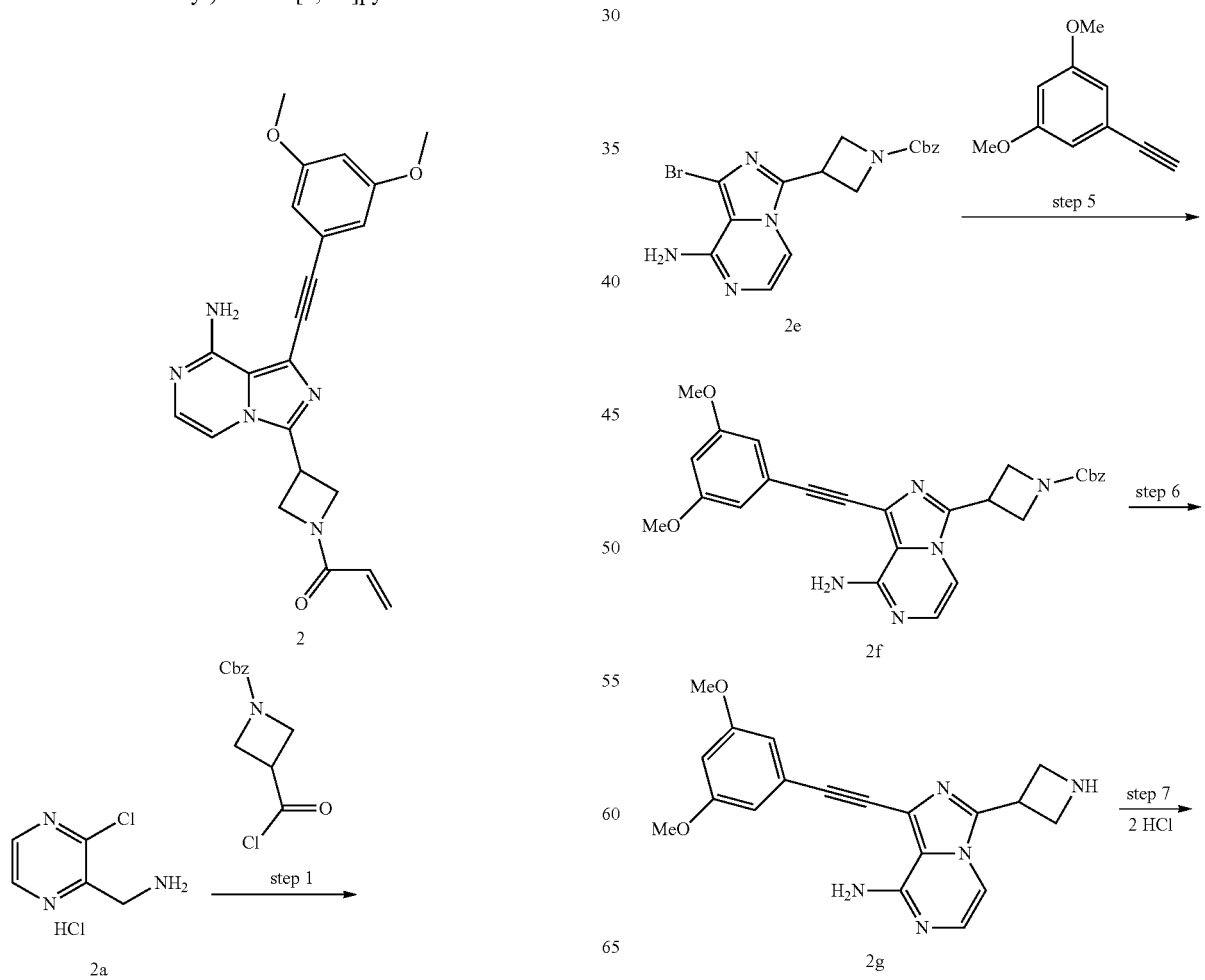

-continued

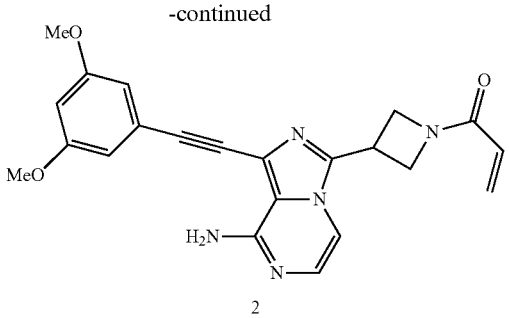

2

Step 1

Benzyl-3-(((3-chloropyrazin-2-yl)methyl)carbamoyl) azetidine-1-carboxylate

To a solution of (3-chloropyrazin-2-yl)methanamine hydrochloride 1a (0.9 g, 5.0 mmol) and N,N-dimethyl formamide (0.02 mL) in dichloromethane (20 mL) at room temperature, was added dropwise a solution of benzyl 3-(chlorocarbonyl)azetidine-1-carboxylate (1.3 g, 5.0 mmol) in dichloromethane (5.0 mL) at room temperature. The resulting mixture was stirred at room temperature for 10 min. The reaction mixture was quenched with saturated sodium bicarbonate solution (30 mL) and the organic phase was separated. The aqueous phase was extracted with dichloromethane (30 mL×2). The combined organic phase was washed with saturated brine (30 mL×2), dried over anhydrous sodium sulfate and filtered. The filtrate was concentrated under vacuum and the residue was purified by flash column chromatography (20:1 dichloromethane/methanol) to provide benzyl-3-(((3-chloropyrazin-2-yl)methyl)carbamoyl)azetidine-1-carboxylate 2a (1.20 g, 3.7 mmol, yellow oil). Yield: 75%.

$^1$H NMR (400 MHz, CDCl$_3$) δ8.43 (d, J=2.4 Hz, 1H), 8.34 (d, J=2.4 Hz, 1H), 7.35-7.27 (m, 5H), 6.91 (bs, 1H), 5.10 (s, 2H), 4.71 (d, J=4.4 Hz, 2H), 4.27-4.19 (m, 4H), 3.40 (dd, J=6.0 & 6.0 Hz, 1H).

Step 2

Benzyl-3-(8-chloroimidazo[1,5-a]pyrazin-3-yl)azetidine-1-carboxylate

To a solution of benzyl-3-(((3-chloropyrazin-2-yl)methyl) carbamoyl)azetidine-1-carboxylate 2b (0.48 g, 1.5 mmol) in acetonitrile (15 mL) at room temperature, was added dropwise pyridine (1.20 g, 15.0 mmol). Under nitrogen protection, the resulting mixture was added dropwise phosphorus oxychloride (1.15 g, 7.5 mmol) and stirred at room temperature for 0.5 h. The mixture was concentrated under vacuum to remove the solvent. The residue was neutralized by saturated sodium bicarbonate solution and extracted with dichloromethane (50 mL×3). The combined organic phase dried over anhydrous sodium sulfate and filtered. The filtrate was concentrated under vacuum and the residue was purified by flash column chromatography (3:1-1:2 hexane/ethyl acetate) to provide benzyl-3-(8-chloroimidazo[1,5-a]pyrazin-3-yl)azetidine-1-carboxylate 2b (0.37 g, 1.1 mmol, yellow oil). Yield: 72%.

MS m/z (ESI): 343 & 345 [M+1].

Step 3

Benzyl-3-(1-bromo-8-chloroimidazo[1,5-a]pyrazin-3-yl)azetidine-1-carboxylate

A suspension of benzyl-3-(8-chloroimidazo[1,5-a]pyrazin-3-yl)azetidine-1-carboxylate 2c (0.118 g, 0.36 mmol), N-bromosuccinimide (0.71 g, 4.0 mmol) in N,N-dimethylformamide (1.5 mL) was stirred at room temperature for 1 h. The reaction was quenched with saturated sodium thiosulfate solution and extracted with dichloromethane (30 mL×4). The combined organic phase was dried over anhydrous sodium sulfate and filtered. The filtrate was concentrated under vacuum and the residue was purified by preparative-TLC (1:1 hexane/ethyl acetate) to provide the title compound benzyl-3-(1-bromo-8-chloroimidazo[1,5-a]pyrazin-3-yl)azetidine-1-carboxylate 2c (0.143 g, 0.34 mmol, yellow oil). Yield: 94%.

MS m/z (ESI): 421 & 423 [M+1].

Step 4

Benzyl-3-(8-amino-1-bromoimidazo[1,5-a]pyrazin-3-yl)azetidine-1-carboxylate

In a sealed tube (120 mL) benzyl-3-(1-bromo-8-chloroimidazo[1,5-a]pyrazin-3-yl)azetidine-1-carboxylate 2f (0.143 g, 0.34 mmol) was solved in isopropanol (10 mL), and then ammonium hydroxide (30% aqueous solution, 2 mL) was added dropwise with stirring. The tube was sealed and the mixture was heated to 100° C. and stirred for 6 h. The mixture was cooled to room temperature and concentrated under vacuum. The residue was purified by preparative-TLC (19:1 dichloromethane/methanol) to provide benzyl-3-(8-amino-1-bromoimidazo[1,5-a]pyrazin-3-yl) azetidine-1-carboxylate 2e (0.123 g, 0.31 mmol, yellow oil). Yield: 90%.

MS m/z (ESI): 402 & 404 [M+1].

Step 5

Benzyl-3-(8-amino-1-((3,5-dimethoxyphenyl)ethynyl)imidazo [1,5-a]pyrazin-3-yl)azetidine-1-carboxylate To a solution of benzyl-3-(8-amino-1-bromoimidazo[1,5-a]pyrazin-3-yl)azetidine-1-carboxylate 2e (0.123 g, 0.31 mmol), 1-ethynyl-3,5-dimethoxybenzene (0.740 g, 3.10 mmol) and triethylamine (0.310 g, 3.10 mmol) in N,N-dimethylformamide (5 mL), under nitrogen protection, were added cuprous iodide (12 mg, 0.06 mmol) and 1,1'-bis (diphenylphosphino)ferrocene-palladium(II) dichloride (22 mg, 0.03 mmol). The mixture was heat to 80° C. and stirred for 5 h. The mixture was cooled to room temperature, quenched with saturated ammonium chloride solution (10 mL) and extracted with dichloromethane (50 mL×3). The combined organic phase was washed with brine (20 mL×2), dried over anhydrous sodium sulfate and filtered. The residue was purified by preparative-TLC (19:1 dichloromethane/methanol) to provide benzyl-3-(8-amino-1-((3,5-dimethoxyphenyl)ethynyl)imidazo [1,5-a]pyrazin-3-yl)azetidine-1-carboxylate 2f (52.5 mg, 0.11 mmol, grey solid), yield: 35%.

MS m/z (ESI): 484 [M+1].

Step 6

1-((3,5-dimethoxyphenyl)ethynyl)-3-(azetidin-3-yl) imidazo [1,5-a]pyrazin-8-amine hydrochloride salt A suspension of benzyl-3-(8-amino-1-((3,5-dimethoxyphenyl)ethynyl)imidazo[1,5-a]pyrazin-3-yl)azetidine-1-carboxylate 2f (10.5 mg, 0.02 mmol, grey solid) in hydrochloric acid (37% aqueous solution, 1 mL) was stirred at room temperature for 3 h. The reaction was diluted with ultrapure water (5 mL) and washed with diethyl ether (5 mL). The aqueous phase was concentrated under vacuum to provide 1-((3,5-dimethoxyphenyl)ethynyl)-3-(azetidin-3-yl)imidazo[1,5-a]pyrazin-8-amine hydrochloride salt 2g (11.3 mg, 0.027 mmol, yellow solid), yield: 100%.

MS m/z (ESI): 350 [M+1].

Step 7

1-((3,5-Dimethoxyphenyl)ethynyl)-3-(1-acrylazacyclobutan-3-yl)imidazo[1,5-a]pyrazin-8-amine A suspension of 1-((3,5-dimethoxyphenyl)ethynyl)-3-(azetidin-3-yl)imidazo[1,5-a]Pyrazin-8-amine hydrochloride salt 2g (11.3 mg, 0.027 mmol) and triethylamine (20 mg, 0.20 mmol) in anhydrous N,N-dimethylacetamide (1.0 mL) and anhydrous tetrahydrofuran (1.2 mL) was stirred at 0° C. for 10 min. Under nitrogen protection, a solution of acryloyl chloride (2 mg, 0.022 mmol) in anhydrous tetrahydrofuran (1.0 mL) was added dropwise with vigorous stirring. The mixture was stirred for 2 min, quenched with saturated sodium bicarbonate aqueous solution (10 mL) and extracted with dichloromethane (30 mL×3). The combined organic phase was dried over anhydrous sodium sulfate and filtered. The residue was purified by preparative-TLC (20:1 dichloromethane/methanol) to provide 1-((3,5-dimethoxyphenyl)ethynyl)-3-(1-acrylazacyclobutan-3-yl)imidazo[1,5-a]pyrazin-8-amine 2 (5.5 mg, 0.014 mmol, white solid). Yield: 70%.

MS m/z (ESI): 404 [M+1];

$^1$H NMR (400 MHz, CDCl$_3$) δ7.16-7.12 (m, 1H), 7.10-7.07 (m, 1H), 6.72 (s, 2H), 6.51 (s, 1H), 6.37 (d, J=17.2 Hz, 1H), 6.24 (t, J=17.2 Hz, 1H), 6.06-5.78 (bs, 2H), 5.72 (d, J=17.2 Hz, 1H), 4.90-4.82 (m, 1H), 4.66 (t, J=8.8 Hz, 1H), 4.57 (t, J=8.8 Hz, 1H), 4.40-4.29 (m, 1H), 4.18-4.06 (m, 1H), 3.81 (s, 6H).

Example 3

(R)-1-((3,5-Dimethoxyphenyl)ethynyl)-3-(1-acrylpyrrolidin-3-yl)imidazo[1,5-a]pyrazin-8-amine

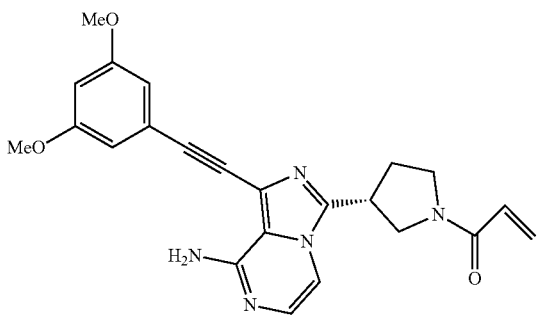

3

(R)-1-((3,5-Dimethoxyphenyl)ethynyl)-3-(1-acrylpyrrolidin-3-yl)imidazo[1,5-a]pyrazin-8-amine 3 was prepared according to the steps of Example 1 by replacing (S)-1-((benzyloxy)carbonyl)pyrrolidine-3-carboxylic acid with (R)-1-((benzyloxy)carbonyl)pyrrolidine-3-carboxylic acid at the first step in Example 1.

MS m/z (ESI): 418 [M+1];

$^1$H NMR (400 MHz, CDCl$_3$) δ7.24-7.11 (m, 2H), 6.71 (s, 2H), 6.50-6.37 (m, 3H), 6.19-5.84 (bs, 2H), 5.78-5.70 (m, 1H), 4.16-4.07 (m, 2H), 3.96-3.93 (m, 1H), 3.80 (s, 6H), 3.80-3.61 (m, 2H), 2.46-2.22 (m, 2H).

Example 4

1-((3,5-Dimethoxyphenyl)ethynyl)-3-(1-acrylpyrrolidin-3-yl)imidazo[1,5-a]pyrazin-8-amine

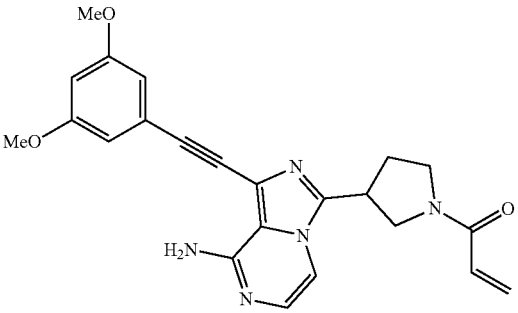

4

1-((3,5-Dimethoxyphenyl)ethynyl)-3-(1-acrylpyrrolidin-3-yl)imidazo[1,5-a]pyrazin-8-amine 4 was prepared according to the steps of Example 1 by replacing (S)-1-((benzyloxy)carbonyl)pyrrolidine-3-carboxylic acid with 1-((benzyloxy)carbonyl)pyrrolidine-3-carboxylic acid at the first step in Example 1.

MS m/z (ESI): 418 [M+1];

$^1$H NMR (400 MHz, CDCl$_3$) δ7.24-7.04 (m, 2H), 6.71 (d, J=2.0 Hz, 2H), 6.51-6.48 (m, 1H), 6.51-6.32 (m, 2H), 6.19-5.84 (bs, 2H), 5.75-5.65 (m, 1H), 4.24-4.03 (m, 2H), 4.02-3.89 (m, 1H), 3.81 (s, 6H), 3.80-3.61 (m, 2H), 2.55-2.16 (m, 2H).

Example 5

(R)-1-((3,5-Dimethoxyphenyl)ethynyl)-3-(1-butan-2-ynoylpyrrolidin-3-yl)imidazo[1,5-a]pyrazin-8-amine

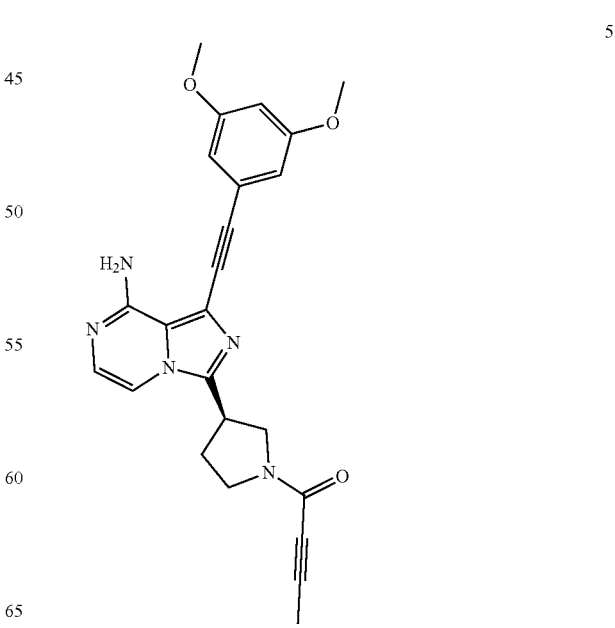

5

(R)-1-((3,5-Dimethoxyphenyl)ethynyl)-3-(1-butan-2-ynoylpyrrolidin-3-yl)imidazo[1,5-a]pyrazin-8-amine 5 was prepared according to the steps of Example 3 but by replacing acryloyl chloride with but-2-ynoyl chloride at the seventh step in Example 3.

MS m/z (ESI): 430 [M+1];
$^1$H NMR (400 MHz, CDCl$_3$) δ7.23-7.12 (m, 2H), 6.72 (s, 2H), 6.50 (s, 1H), 6.20-5.80 (br, 2H), 4.24-3.99 (m, 3H), 3.81 (s, 6H), 3.74-3.60 (m, 2H), 2.44-2.34 (m, 2H), 2.04-1.95 (m, 3H).

Example 6

(R)-(E)-1-((3,5-Dimethoxyphenyl)ethynyl)-3-(1-butan-2-enoylpyrrolidin-3-yl)imidazo[1,5-a]pyrazin-8-amine

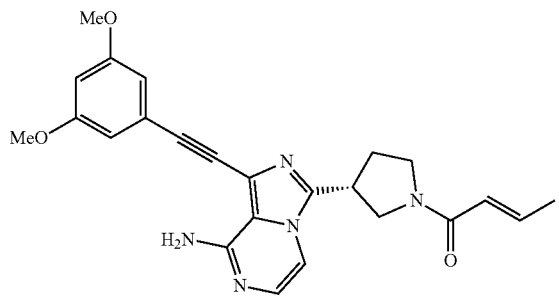

6

(R)-(E)-1-((3,5-Dimethoxyphenyl)ethynyl)-3-(1-butan-2-enoylpyrrolidin-3-yl)imidazo[1,5-a]pyrazin-8-amine 6 was prepared according to the steps of Example 3 by replacing acryloyl chloride with 2-butenoyl chloride at the seventh step in Example 3.

MS m/z (ESI): 432 [M+1];
$^1$H NMR (400 MHz, CDCl$_3$) δ7.23-7.14 (m, 2H), 6.98-6.96 (m, 1H), 6.72 (s, 2H), 6.50 (s, 1H), 6.16 (d, J=15.2 Hz, 1H), 5.95 (bs, 2H), 4.13-3.94 (m, 3H), 3.81 (s, 6H), 3.73-3.63 (m, 2H), 2.45-2.30 (m, 2H), 1.91-1.87 (m, 3H).

Example 7

(E)-1-((3,5-Dimethoxyphenyl)ethynyl)-3-(1-butan-2-enoylpyrrolidin-3-yl)imidazo[1,5-a]pyrazin-8-amine

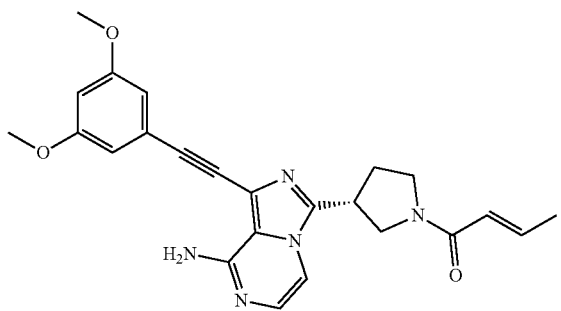

7

(E)-1-((3,5-Dimethoxyphenyl)ethynyl)-3-(1-butan-2-enoylpyrrolidin-3-yl)imidazo[1,5-a]pyrazin-8-amine 7 was prepared according to the steps of Example 4 but by replacing acryloyl chloride with 2-butenoyl chloride at the seventh step in Example 4.

MS m/z (ESI): 432 [M+1];
$^1$H NMR (400 MHz, CDCl$_3$) δ7.23-7.14 (m, 2H), 6.98-6.96 (m, 1H), 6.72 (s, 2H), 6.50 (s, 1H), 6.16 (d, J=7.6 Hz, 1H), 5.99-5.91 (br, 2H), 4.13-3.94 (m, 3H), 3.81 (s, 6H), 3.73-3.63 (m, 2H), 2.45-2.30 (m, 2H), 1.91-1.87 (m, 3H).

Example 8

1-((3,5-Dimethoxyphenyl)ethynyl)-3-(1-propynoylpyrrolidin-3-yl)imidazo[1,5-a]pyrazin-8-amine

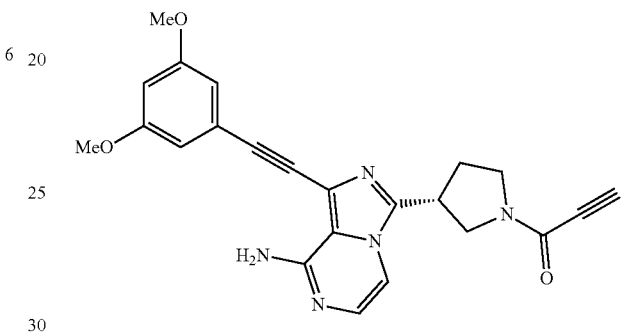

8

1-((3,5-Dimethoxyphenyl)ethynyl)-3-(1-propynoylpyrrolidin-3-yl)imidazo[1,5-a]pyrazin-8-amine 8 was prepared according to the steps of Example 4 but by replacing acryloyl chloride with propioloyl chloride at the seventh step in Example 4.

MS m/z (ESI): 416 [M+1].

Example 9

1-((3,5-Dimethoxyphenyl)ethynyl)-3-(1-butan-2-ynoylpyrolidin-3-yl)imidazo[1,5-a]pyrazin-8-amine

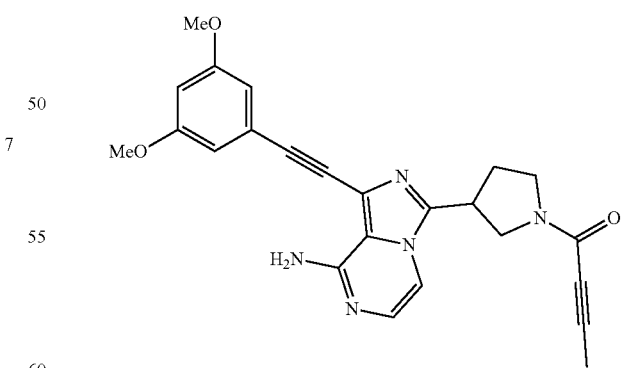

9

1-((3,5-Dimethoxyphenyl)ethynyl)-3-(1-butan-2-ynoylpyrolidin-3-yl)imidazo[1, 5-a]pyrazin-8-amine 9 was prepared according to the steps of Example 4 but by replacing acryloyl chloride with but-2-ynoyl chloride at the seventh step in Example 4.

MS m/z (ESI): 430 [M+1];

¹H NMR (400 MHz, CDCl₃) δ7.23-7.14 (m, 2H), 6.72 (s, 2H), 6.50 (s, 1H), 5.88 (br, 2H), 4.24-4.02 (m, 3H), 3.81 (s, 6H) 3.88-3.60 (m, 2H), 2.44-2.39 (m, 2H), 2.05 (s, 3H).

Example 10

(E)-1-((3,5-Dimethoxyphenyl)ethynyl)-3-(1-(4-dimethylamino))butan-2-enoylpyrrolidin-3-yl)imidazo[1,5-a]pyrazin-8-amine

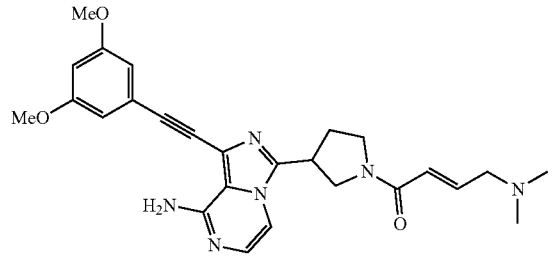

(E)-1-((3,5-Dimethoxyphenyl)ethynyl)-3-(1-(4-dimethylamino))butan-2-enoylpyrrolidin-3-yl)imidazo[1,5-a]pyrazin-8-amine 10 was prepared according to the steps of Example 4 by replacing acryloyl chloride with (E)-4-(dimethylamino)but-2-enoyl chloride at the seventh step in Example 4.

MS m/z (ESI): 475 [M+1];
¹H NMR (400 MHz, CDCl₃) δ7.20-7.16 (m, 2H), 6.98-6.90 (m, 1H), 6.71 (s, 2H), 6.50 (s, 1H), 6.45 (s, 1H), 5.85-5.78 (br, 2H), 4.13-4.11 (m, 2H), 3.97-3.94 (m, 3H), 3.81 (s, 6H), 3.76-3.77 (m, 2H), 2.30-2.28 (m, 8H).

Example 11

(E)-1-((3,5-Dimethoxyphenyl)ethynyl)-3-(1-but-2-enoylazacyclobutan-3-yl)imidazo[1,5-a]pyrazin-8-amine

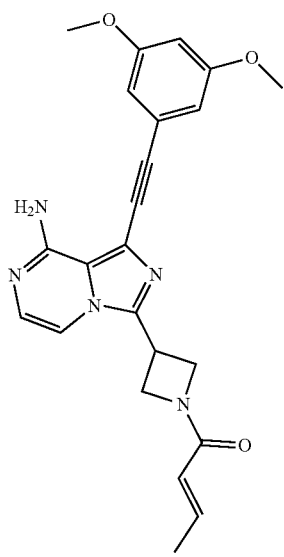

(E)-1-((3,5-Dimethoxyphenyl)ethynyl)-3-(1-but-2-enoylazacyclobutan-3-yl)imidazo[1,5-a]pyrazin-8-amine 11 was prepared according to the steps of Example 2 but by replacing acryloyl chloride with 2-butenoyl chloride at the seventh step in Example 2.

MS m/z (ESI): 418 [M+1];
¹H NMR (400 MHz, CDCl₃) δ7.14-7.12 (m, 1H), 7.09-7.07 (m, 1H), 7.02-6.82 (m, 1H), 6.72 (s, 2H), 6.51 (s, 1H), 6.18-5.85 (m, 2H), 5.36-5.33 (m, 1H), 4.84-4.80 (m, 1H), 4.64-4.61 (m, 1H), 4.55-4.50 (m, 1H), 4.38-4.26 (m, 1H), 4.18-4.03 (m, 1H), 3.81 (s, 6H), 1.89 (d, J=5.2 Hz, 3H).

Example 12

1-((3,5-Dimethoxyphenyl)ethynyl)-3-(1-but-2-ynoylazacyclo butan-3-yl)imidazo[1,5-a]pyrazin-8-amine

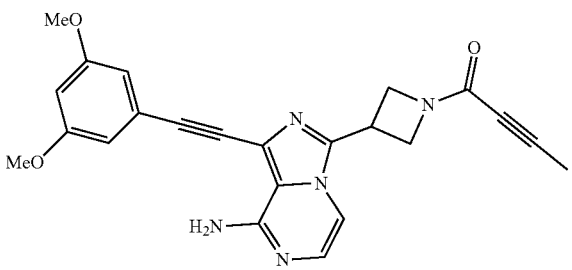

1-((3,5-Dimethoxyphenyl)ethynyl)-3-(1-but-2-ynoylazacyclo butan-3-yl)imidazo[1,5-a]pyrazin-8-amine 12 was prepared according to the steps of Example 2 by replacing acryloyl chloride with but-2-ynoyl chloride at the seventh step in Example 2.

MS m/z (ESI): 416 [M+1];
¹H NMR (400 MHz, CDCl₃) δ7.15 (d, J=2.8, 1H), 7.08 (d, J=2.8, 1H), 6.72 (s, 2H), 6.51 (s, 1H), 5.86-5.82 (br, 2H), 4.79-4.71 (m, 1H), 4.61 (t, J=8.4 Hz, 1H), 4.50 (t, J=8.4 Hz, 1H), 4.38 (t, J=8.8 Hz, 1H), 4.17-4.05 (m, 1H), 3.81 (s, 6H), 1.99 (s, 3H).

Biological Experiment

FGFR1 Activity Inhibition Test

The influence of the compound according to the present invention on the tyrosine kinase activity of fibroblast growth factor receptor 1 (FGFR1) was evaluated by an in vitro kinase assay experiment.

The experimental method is summarized as follows:

The in vitro activity of FGFR1 was determined by assaying the phosphorylation level of the substrate in the kinase reaction, by means of an HTRF (Homogeneous Time-Resolve Fluorescence) kinase assay kit. The reaction buffer comprised the following components: 5-fold diluted enzymatic buffer/kinase 5× (Cisbio, Catalog number 62EZBFDD) (major ingredient: 50 mM HEPES, pH 7.0), 5 mM MgCl₂, 1 mM DTT; the human recombinant FGFR1 catalytic structural domain protein (amino acids 308-731) was purchased from Tsinghua Protein Purification and Characterization Center, located in Zheng Yutong Building, Tsinghua University, diluted with the reaction buffer to a 0.6 ng/μL kinase solution; the substrate reaction solution comprised a biotin labeled tyrosine kinase substrate diluted with the reaction buffer to 400 nM (Cisbio, catalog number 62TKOPEC), and 40 μM ATP, and the assay solution comprised an Eu³⁺ labeled cage-shaped antibody (Cisbio, Catalog number 61T66KLB) diluted with the assay buffer (Cisbio, Catalog number 62SDBRDF) to 0.125 ng/μL, and 25 nM streptavidin labeled XL665 (Cisbio, Catalog number 610SAXLB).

The compound was dissolved and diluted in 100% DMSO to 1 mM, then 4-fold-series diluted with DMSO to a minimum concentration of 0.061 μM, and each concentration point was then 40-fold diluted with the reaction buffer. If the $IC_{50}$ value of the compound was very low, the initial concentration of the compound could be reduced.

4 μL of a compound solution and 2 μL of an FGFR1 kinase solution were added into a 384 well assay plate (Thermofish, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the $Eu^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision (Perkin Elmer, company located in Limon City, Calif., USA). The ratio of 665/620 is in positive correlation to the phosphorylation degree of the substrate, thereby to detect the FGFR1 kinase activity. In this experiment, the group without the FGFR1 protein added was used as a negative control (100% inhibition), and the group with the FGFR1 protein but without the compound added was used as a positive control (0% inhibition). The inhibition percentage of the compound against FGFR1 activity could be calculated with the following formula:

Inhibition percentage=100−100*($signal_{compound}$−$signal_{negative\ control}$)/($signal_{positive\ control}$−$signal_{negative\ control}$)

The $IC_{50}$ value of the compound was calculated by the following formula, from 10 concentration points, with software XLfit (ID Business Solutions Ltd., UK):

Y=Bottom+(Top−Bottom)/(1+10^((Log $IC_{50}$−X)*slope factor))

Where, Y is the inhibition percentage, Bottom is the bottom plateau value of the S-type curve, Top is the top plateau value of the S-type curve, X is the log value of the compound concentration to be measured, and slope factor is the slope coefficient of the curve.

FGFR2 Activity Inhibition Test

The influence of the compound according to the present invention on the activity of fibroblast growth factor receptor 2 (FGFR2) was evaluated by an in vitro kinase assay experiment.

The experimental method is summarized as follows:

The in vitro activity of FGFR2 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM $MgCl_2$, 1 mM DTT; the human recombinant FGFR2 catalytic structural domain protein (amino acids 400-821) was commercially available from Beijing Sino Biological Inc. (Zhonghe Street 14, B-203, Beijing Economic and Technological Development Zone, 4008909989), diluted with the reaction buffer to a 0.045 ng/μL kinase solution; the substrate reaction solution comprised a biotin labeled tyrosine kinase substrate diluted with the reaction buffer to 800 nM (Cisbio, catalog number 62TKOPEC), and 50 μM ATP, and the assay solution comprised an $Eu^{3+}$ labeled cage-shaped antibody (Cisbio, Catalog number 61T66KLB) diluted with the assay buffer (Cisbio, Catalog number 62SDBRDF) to 0.125 ng/μL, and 50 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the $IC_{50}$ value of the compound was very low, the initial concentration of the compound could be reduced.

4 μL of a compound solution and 2 μL of an FGFR2 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the $Eu^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision (Perkin Elmer, company located in in Limon City, Calif., USA). The ratio of 665/620 is in positive correlation to the phosphorylation degree of the substrate, thereby to detect the FGFR2 kinase activity. In this experiment, the group without the FGFR2 protein added was used as a negative control (100% inhibition), and the group with the FGFR2 protein but without the compound added was used as a positive control (0% inhibition). The inhibition percentage of the compound against FGFR2 activity could be calculated with the following formula:

Inhibition percentage=100−100*($signal_{compound}$−$signal_{negative\ control}$)/($signal_{positive\ control}$−$signal_{negative\ control}$)

The $IC_{50}$ value of the compound was calculated by the following formula, from 10 concentration points, with software XLfit (ID Business Solutions Ltd., UK):

Y=Bottom+(Top−Bottom)/(1+10^((Log $IC_{50}$−X)*slope factor))

Where, Y is the inhibition percentage, Bottom is the bottom plateau value of the S-type curve, Top is the top plateau value of the S-type curve, X is the log value of the compound concentration to be measured, and slope factor is the slope coefficient of the curve.

FGFR3 Activity Inhibition Test

The influence of the compound according to the present invention on the activity of fibroblast growth factor receptor 3 (FGFR3) was evaluated by an in vitro kinase assay experiment.

The experimental method is summarized as follows:

The in vitro activity of FGFR3 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM $MgCl_2$, 1 mM DTT; the human recombinant FGFR3 catalytic structural domain protein (amino acids 399-806) was commercially available from Sino Biological Inc. (Zhonghe Street 14, Beijing Economic and Technological Development Zone), diluted with the reaction buffer to a 0.3 ng/μL kinase solution; the substrate reaction solution comprised a biotin labeled tyrosine kinase substrate diluted with the reaction buffer to 1000 nM (Cisbio, catalog number 62TKOPEC), and 90 μM ATP, and the assay solution comprised an $Eu^{3+}$ labeled cage-shaped antibody (Cisbio, Catalog number 61T66KLB) diluted with the assay buffer (Cisbio, Catalog number 62SDBRDF) to 0.125 ng/μL, and 62.5 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the $IC_{50}$ value of the compound was very low, the initial concentration of the compound could be reduced.

4 μL of a compound solution and 2 μL of an FGFR3 kinase solution were added into a 384 well assay plate (Thermofish, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the $Eu^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision (Perkin Elmer, company located in Limon City, Calif., USA). The ratio of 665/620 is in positive correlation to the phosphorylation degree of the substrate, thereby to detect the FGFR3 kinase activity. In this experiment, the group without the FGFR3 protein added was used as a negative control (100% inhibition), and the group with the FGFR3 protein but without the compound added was used as a positive control (0% inhibition). The inhibition percentage of the compound against FGFR3 activity could be calculated with the following formula:

Inhibition percentage=100−100*($signal_{compound}$−$signal_{negative\ control}$)/($signal_{positive\ control}$−$signal_{negative\ control}$)

The $IC_{50}$ value of the compound was calculated by the following formula, from 10 concentration points, with software XLfit (ID Business Solutions Ltd., UK):

Y=Bottom+(Top−Bottom)/(1+10^((Log $IC_{50}$−X)*slope factor))

Where, Y is the inhibition percentage, Bottom is the bottom plateau value of the S-type curve, Top is the top plateau value of the S-type curve, X is the log value of the compound concentration to be measured, and slope factor is the slope coefficient of the curve.

FGFR4 Activity Inhibition Test

The influence of the compound according to the present invention on the activity of fibroblast growth factor receptor 4 (FGFR4) was evaluated by an in vitro kinase assay experiment.

The experimental method is summarized as follows:

The in vitro activity of FGFR4 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM $MgCl_2$, 1 mM DTT; the human recombinant FGFR4 catalytic structural domain protein (amino acids 460-802) was commercially available from Tsinghua Protein Purification and Characterization Center, diluted with the reaction buffer to a 0.5 ng/μL kinase solution; the substrate reaction solution comprised a biotin labeled tyrosine kinase substrate diluted with the reaction buffer to 500 nM (Cisbio, catalog number 62TKOPEC), and 90 μM ATP, and the assay solution comprised an $Eu^{3+}$ labeled cage-shaped antibody (Cisbio, Catalog number 61T66KLB) diluted with the assay buffer (Cisbio, Catalog number 62SDBRDF) to 0.125 ng/μL, and 31.25 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the $IC_{50}$ value of the compound was very low, the initial concentration of the compound could be reduced.

4 μL of a compound solution and 2 μL of an FGFR4 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the $Eu^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision (Perkin Elmer, located in Limon City, Calif., USA). The ratio of 665/620 is in positive correlation to the phosphorylation degree of the substrate, thereby to detect the FGFR4 kinase activity. In this experiment, the group without the FGFR4 protein added was used as a negative control (100% inhibition), and the group with the FGFR4 protein but without the compound added was used as a positive control (0% inhibition). The inhibition percentage of the compound against FGFR4 activity could be calculated with the following formula:

Inhibition percentage=100−100*($signal_{compound}$−$signal_{negative\ control}$)/($signal_{positive\ control}$−$signal_{negative\ control}$)

The $IC_{50}$ value of the compound was calculated by the following formula, from 10 concentration points, with software XLfit (ID Business Solutions Ltd., UK):

Y=Bottom+(Top−Bottom)/(1+10^((Log $IC_{50}$−X)*slope factor))

Where, Y is the inhibition percentage, Bottom is the bottom plateau value of the S-type curve, Top is the top plateau value of the S-type curve, X is the log value of the compound concentration to be measured and slope factor is the slope coefficient of the curve.

| The kinase assay results: A < 50 nM, B: 50-500 nM, C: 500-1000 nM | | | | |
|---|---|---|---|---|
| Compound No. | FGFR1 IC$_{50}$ (nM) | FGFR2 IC$_{50}$ (nM) | FGFR3 IC$_{50}$ (nM) | FGFR4 IC$_{50}$ (nM) |
| 1 | B | A | A | B |
| 2 | B | A | A | A |
| 3 | B | A | A | B |
| 4 | A | A | A | B |
| 5 | C | A | A | C |
| 6 | ND | A | A | C |
| 7 | ND | A | A | ND |
| 8 | B | A | B | B |
| 9 | ND | A | B | ND |
| 10 | ND | A | A | ND |
| 11 | ND | B | B | ND |
| 12 | ND | B | B | ND |

*ND = Not detected

RT4 Cell Proliferation Inhibition Test

The effects of the compounds of the present invention on the proliferation of RT4 bladder cancer cells were evaluated by using the luminescent cell viability test experiment. The experimental method is summarized as follows: A CellTilter-Glo (CTG) assay kit was used to detect an indicator ATP of active cellular metabolism by means of a unique stable luciferase, and the luminous signal produced in the test was in direct proportion to the count of active cells in the medium, thereby to detect the RT4 cell proliferation.

A CellTilter-Glo agent (Promega, G7572) was comprised of a CTG lyophilized powder and a CTG buffer, and the lyophilized powder was dissolved into the buffer in use.

RT4 bladder cancer cells (cell source: Shanghai Academy of Life Sciences, Chinese Academy of Sciences) were cultured in a DMEM complete medium (Thermofisher, 11995073) containing a 10% FBS (GBICO, 10099-141) and 100 units/ml mycillin mixed solution (Thermofisher, 15140122). When the cells coverage reached 80-90% in the culture vessel, after the cells were digested and blown about with 0.25% pancreatin (containing EDTA) (Thermofisher, 25200056), they were planted in a white 384 well plate (Thermofisher, 164610), with 1000 cells in each well (27 μl of a DMEM complete medium), and then the 384 well plate was placed into an incubator at 37° C. and 5% CO$_2$ and cultured overnight (18-20 h). The compound was dissoved and diluted in 100% DMSO to 5 mM, and then 4-fold series diluted with DMSO to a minimum concentration of 0.061 μM and each concentration point was 50 fold diluted with FBS free DMEM medium. If the 1050 value of the compound is very low, the initial concentration of the compound could be reduced. After the overnight culture, 3 μl of the DMEM diluted compound was added into each well, and gently centrifugated and mixed uniformly. The group with 10 μM TAS-120((S)-1-((3,5-dimethoxyphenyl)ethynyl)-3-(1-acryloyl pyrrolidine-3-yl)-1H-pyrazolo [3,4-d]pyrimidine-8-amine, PCT Int. Appl., 2015008844) added served as a negative control (100% inhibition), and a 0.2% DMSO group served as a positive control (0% inhibition). This 384 well plate was placed into an incubator at 37° C. and 5% CO$_2$ for further culture, taken out after 72 h, and stood at room temperature for 30 min. The CTG agent was also taken out and balanced to room temperature. 15 μl of the CTG agent was added into each well, and placed onto a shaker to be gently shaken for 3 min to ensure sufficient cell lysis. After 10 min of standing to allow the luminescence signal to be stable, the luminescence signal was read with EnVision (Perkin Elmer, located in Limon City, Calif., USA).

The inhibition percentage of the compound against RT4 cell proliferation could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 8 concentration points, with software XLfit (ID Business Solutions Ltd., UK):

Y=Bottom+(Top−Bottom)/(1+10^((Log IC$_{50}$−X)*slope factor))

Where, Y is the inhibition percentage, Bottom is the bottom plateau value of the S-type curve, Top is the top plateau value of the S-type curve, X is the log value of the compound concentration to be measured, and slope factor is the slope coefficient of the curve.

| The RT4 cell proliferation Inhibition test results: A < 100 nM, B: 100-500 nM | |
|---|---|
| Compound No. | RT4 IC$_{50}$ (nM) |
| 1 | A |
| 2 | B |
| 4 | B |

Hep3B Cell Proliferation Inhibition Test

The influence of the compound according to the present invention on Hep3B cell proliferation was evaluated by a luminescence cell viability test.

The experimental method is summarized as follows:

A CellTilter-Glo (CTG) assay kit was used to detect an indicator ATP of active cellular metabolism by means of a unique stable luciferase, and the luminous signal produced in the test was in direct proportion to the count of active cells in the medium, thereby to detect the cell proliferation of Hep3B.

A CellTilter-Glo reagent (Promega, G7572) was comprised of a CellTilter-Glo lyophilized powder and a CellTilter-Glo buffer, and the lyophilized powder was dissolved into the buffer in use.

Hep3B cells (ATCC, HB-8064) (cell source: Shanghai Academy of Life Sciences, Chinese Academy of Sciences) were cultured in a DMEM complete medium (Thermofisher, 11995073) containing a 10% FBS (GBICO, 10099-141) and 100 units/ml mycillin mixed solution (Thermofisher, 15140122). When the cells coverage reached 80-90% in the culture vessel, after the cells were digested and blown about with 0.25% pancreatin (containing EDTA) (Thermofisher, 25200056), they were planted in a white 384 well plate (Thermofisher, 164610), with 1000 cells in each well (27 μl of a DMEM complete medium), and then the 384 well plate was placed into an incubator at 37° C. and 5% CO$_2$ and cultured overnight (18-20 h). The compound was dissolved and diluted in 100% DMSO to 5 mM, then 4-fold-series diluted with DMSO to a minimum concentration of 0.0061 μM, and each concentration point was 50-fold diluted with the FBS-free DMEM medium. If the IC$_{50}$ value of the compound was very low, the initial concentration of the compound could be reduced. After the overnight culture, 3 μl of the DMEM diluted compound was added into each well, and gently centrifugated and mixed uniformly, where a 10 μM BLU9931 group was added to serve as a negative control (100% inhibition) and a 0.2% DMSO group was added to serve as a positive control (0% inhibition). This 384 well plate was placed into an incubator at 37° C. and 5% $CO_2$ for further culture, taken out after 72 h, and stood at room temperature for 30 min. The CTG agent was also taken out and balanced to room temperature. 15 μl of the CTG agent was added into each well, and placed onto a shaker to be gently shaken for 3 min to ensure sufficient cell lysis. After 10 min of standing to allow the luminescence signal to be stable, the luminescence signal was read with EnVision (Perkin Elmer, company located in Limon City, Calif., USA).

The inhibition percentage of the compound against Hep3B cell proliferation could be calculated with the following formula:

Inhibition percentage=100–100*($signal_{compound}$–$signal_{negative\ control}$)/($signal_{positive\ control}$–$signal_{negative\ control}$)

The 1050 value of the compound was calculated by the following formula, from 8 concentration points, with software XLfit (ID Business Solutions Ltd., UK):

Y=Bottom+(Top−Bottom)/(1+10^((Log $IC_{50}$−X)*slope factor))

Where, Y is the inhibition percentage, Bottom is the bottom plateau value of the S-type curve, Top is the top plateau value of the S-type curve, X is the log value of the compound concentration to be measured, and slope factor is the slope coefficient of the curve.

The example compounds of the present invention can effectively inhibit proliferation of Hep3B liver cancer cells, and their IC50s are 100-500 nM.

The invention claimed is:
1. A compound as shown in Formula I:

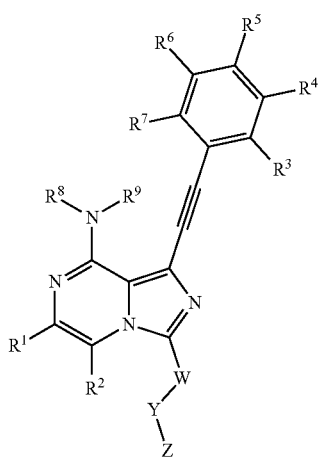

Where $R^1$, $R^2$ are each independently selected from the group consisting of hydrogen, C1-C6 alkyl, halogen and —CN;
$R^3$, $R^4$, $R^5$, $R^6$, $R^7$ are selected from the group consisting of hydrogen, halogen, C1-C6 alkyl, C3-C8 cyclyl, C2-C6 alkynyl, —$OR^{10}$, —C(O)$NR^{10}R^{11}$,
$R^8$, $R^9$ are each independently selected from hydrogen, C1-C6 alkyl;
W is C1-C6 alkyl or absent;
Y is absent or selected from the group consisting of C3-C8 cyclyl, 3-8-membered heterocylcyl, aryl or heteroaryl, where said cyclyl, heterocylyl, aryl and heteroaryl may be optionally substituted with one or more $G^1$;
Z is independently selected from —CN, $NR^{12}$CN,

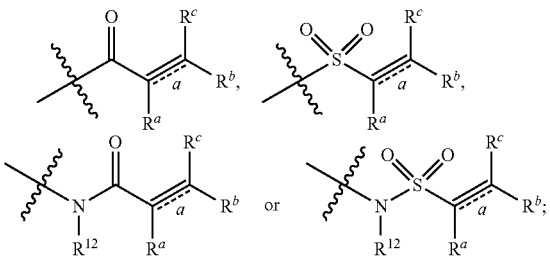

Bond a is a double bond or a triple bond;
When bond a is a double bond, $R^a$, $R^b$ and $R^c$ are each independently selected from the group consisting of hydrogen, —CN, halogen, C1-C6 alkyl, C3-C8 cyclyl or 3-8-membered heterocyclyl, where said alkyl, cyclyl and hetercyclyl may be optionally substituted with one or more $G^2$;
$R^a$ and $R^b$, or $R^b$ and $R^c$ may form a ring containing a heteroatom together with the carbon atoms to which they are attached;
When bond a is a triple bond, $R^a$ and $R^c$ are absent, $R^b$ is independently selected from the group consisting of hydrogen, C1-C6 alkyl, C3-C8 cyclyl, or 3-8-membered heterocyclyl, where said alkyl, cyclyl, and heterocyclyl are optionally substituted by one or more $G^3$;
$R^{10}$, $R^{11}$ and $R^{12}$ are independently selected from the group consisting of hydrogen, C1-C6 alkyl, C3-C8 cyclyl or 3-8-membered heterocyclyl, where said alkyl, cyclyl and heterycyclyl may be optionally substituted with one or more $G^4$;
$G^1$, $G^2$, $G^3$, $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —OC(O)$NR^{13}R^{14}$, —C(O)$OR^{13}$, —C(O)$NR^{13}R^{14}$, —C(O)$R^{13}$, —$NR^{13}R^{14}$, —$NR^{13}$C(O)$R^{14}$, —$NR^{13}$C(O)$NR^{14}R^{15}$, —S(O)$_m R^{13}$ or —$NR^{13}$S(O)$_m R^{14}$, where said alkyl, alkenyl, alkynyl, cyclyl, heterocyclyl, aryl and heteroaryl may be optionally substituted by one or more substituents selected from the group consisting of halogen, —CN, C1-C8 alkyl, C3-C8 cyclyl, 3-8-membered heterocyclyl, —$OR^{13}$, —OC(O)$NR^{13}R^{14}$, —C(O)$OR^{13}$, —C(O)$NR^{13}R^{14}$, —C(O)$R^{13}$, —$NR^{13}R^{14}$, —$NR^{13}$C(O)$R^{14}$, —$NR^{13}$C(O)$NR^{14}R^{15}$, —S(O)$_m R^{13}$ or —$NR^{13}$S(O)$_m R^{14}$;
$R^{13}$, $R^{14}$ and $R^{15}$ are each independently selected from the group consisting of hydrogen, C1-C6 alkyl, 2-6-membered heteroalkyl, C3-C8 cyclyl, 3-8-membered monocyclic heterocylcyl, monocyclic heteroaryl or monocyclic aryl; and m is 1 or 2;
or an isomer, a prodrug, a stable isotopic derivative and a pharmaceutically acceptable salt thereof.

2. The compound according to claim 1, characterized in that the compound as shown in Formula I is of Formula II:

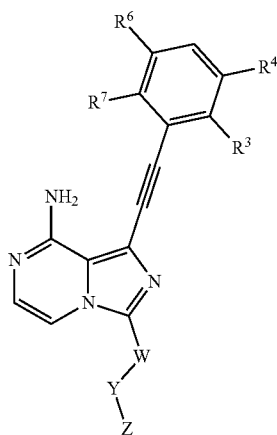

(II)

$R^3$, $R^4$, $R^6$, $R^7$ are selected from the group consisting of hydrogen, halogen, C1-C6 alkyl, C3-C8 cyclyl, C2-C6 alkynyl, —$OR^{10}$, —$C(O)NR^{10}R^{11}$, —$NR^{10}R^{11}$;

W is C1-C6 alkyl or absent;

Y is absent or selected from the group consisting of C3-C8 cyclyl, 3-8-membered heterocyclyl, aryl or heteroaryl, where said cyclyl, heterocyclyl, aryl, and heteroaryl may be optionally substituted by one or more $G^1$;

Z is independently selected from —CN, $NR^{12}$CN,

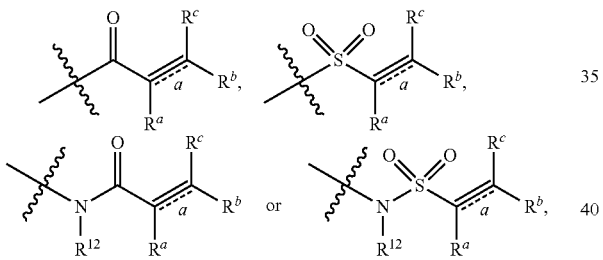

where bond a is a double bond or a triple bond;

When bond a is a double bond, $R^a$, $R^b$ and $R^c$ are each independently selected from the group consisting of hydrogen, —CN, halogen, C1-C6 alkyl, C3-C8 cyclyl or 3-8-membered heterocyclyl, where said alkyl, cyclyl and heterocyclyl may be optionally substituted by one or more $G^2$;

$R^a$ and $R^b$ or $R^b$ and $R^c$ may form a ring containing a hetero atom together with the carbon atoms to which they are attached;

When bond a is a triple bond, $R^a$ and $R^c$ are absent, $R^b$ is independently selected from the group consisting of hydrogen, C1-C6 alkyl, C3-C8 cyclyl or 3-8-membered heterocyclyl, where said alkyl, cyclyl and heterocyclyl may be optionally substituted by one or more $G^3$;

$R^{10}$, $R^{11}$ and $R^{12}$ are independently selected from the group consisting of hydrogen, C1-C6 alkyl, C3-C8 cyclyl or 3-8-membered heterocyclyl, where said alkyl, cyclyl, and heterocyclyl may be optionally substituted by one or more $G^4$;

$G^1$, $G^2$, $G^3$, $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$, where said alkyl, alkenyl, alkynyl, cyclyl, heterocyclyl, aryl, and heteroaryl may be optionally substituted by one or more substituents selected from the group consisting of halogen, —CN, C1-C8 alkyl, C3-C8 cyclyl, 3-8-membered heterocyclyl, —$OR^{13}$, —$OC(O)NR^{13}R^{14}$, —$C(O)OR^{13}$, —$C(O)NR^{13}R^{14}$, —$C(O)R^{13}$, —$NR^{13}R^{14}$, —$NR^{13}C(O)R^{14}$, —$NR^{13}C(O)NR^{14}R^{15}$, —$S(O)_mR^{13}$ or —$NR^{13}S(O)_mR^{14}$;

$R^{13}$, $R^{14}$ and $R^{15}$ are each independently selected from the group consisting of hydrogen, C1-C6 alkyl, 2-6-membered heteroalkyl, C3-C8 cyclyl, 3-8-membered monoheterocyclyl, monocyclic heteroaryl or monocyclic aryl; and m is 1 or 2;

or an isomer, a prodrug, a stable isotopic derivative or a pharmaceutically acceptable salt thereof.

3. The compound according to claim 1, characterized in that the compound as shown in Formula I is of Formula III:

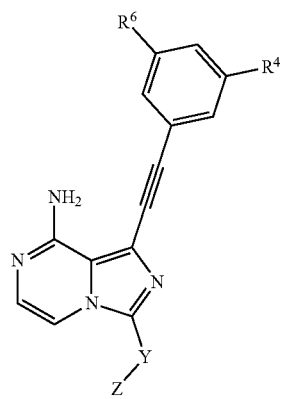

(III)

$R^4$ and $R^6$ are selected from the group consisting of hydrogen, halogen, C1-C6 alkyl, C3-C8 cyclyl, C2-C6 alkynyl, —$OR^{10}$, —$C(O)NR^{10}R^{11}$, and —$NR^{10}R^{11}$;

Y is selected from 3-7 membered heterocyclyl, said heterocyclyl may be optionally substituted by one or more $G^1$;

Z is independently selected from

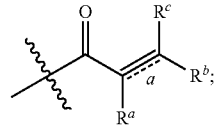

Bond a is a double bond or a triple bond;

When bond a is a double bond, $R^a$, $R^b$ and $R^c$ are each independently selected from the group consisting of hydrogen, —CN, halogen, C1-C6 alkyl, C3-C8 cyclyl or 3-8-membered heterocyclyl, said alkyl, cyclyl, and heterocyclyl may be optionally substituted by, one or more $G^2$;

$R^a$ and $R^b$ or $R^b$ and $R^c$ may form a ring containing a hetero atom together with the carbon atoms to which they are attached;

When bond a is a triple bond, $R^a$ and $R^c$ are absent, $R^b$ is independently selected from the group consisting of hydrogen, C1-C6 alkyl, C3-C8 cyclyl or 3-8-membered heterocyclyl, where said alkyl, cyclyl and heterocyclyl may be optionally substituted by one or more $G^3$;

$R^{10}$ and $R^{11}$ are independently selected from the group consisting of hydrogen, C1-C6 alkyl, C3-C8 cyclyl or 3-8-membered heterocyclyl, where said alkyl, cyclyl, and heterocyclyl may be optionally substituted by one or more $G^4$;

$G^1$, $G^2$, $G^3$, and $G^4$ are each independently selected from the group consisting of halogen, —CN, C1-C6 alkyl, C2-C6 alkenyl, C2-C6 alkynyl, C3-C8 cyclyl, 3-8-membered heterocyclyl, aryl, heteroaryl, —$OR^{13}$, —OC(O)$NR^{13}R^{14}$, —C(O)$OR^{13}$, —C(O)$NR^{13}R^{14}$, —C(O)$R^{13}$, —$NR^{13}R^{14}$, —$NR^{13}$C(O)$R^{14}$, —$NR^{13}$C(O)$NR^{13}R^{14}$, —S(O)$_m R^{13}$ or —$NR^{13}$S(O)$_m R^{14}$, where said alkyl, alkenyl, alkynyl, cyclyl, heterocyclyl, aryl or heteroaryl may be optionally substituted by one or more substituents selected from the group consisting of halogen, —CN, C1-C8 alkyl, C3-C8 cyclyl, 3-8-membered heterocyclyl, —$OR^{13}$, —OC(O)$NR^{13}R^{14}$, —C(O)$OR^{13}$, —C(O)$NR^{13}R^{14}$, —C(O)$R^{13}$, —$NR^{13}R^{14}$, —$NR^{13}$C(O)$R^{14}$, —$NR^{13}$C(O)$NR^{14}R^{15}$, —S(O)$_m R^{13}$ or —$NR^{13}$S(O)$_m R^{14}$;

$R^{13}$, $R^{14}$ and $R^{15}$ are each independently selected from the group consisting of hydrogen, C1-C6 alkyl, 2-6-membered heteroalkyl, C3-C8 cyclyl, 3-8-membered monocyclic heterocylcyl, monocyclic heteroaryl or monocyclic aryl; and m is 1 or 2;

or an isomer, a prodrug, a stable isotopic derivative or a pharmaceutically acceptable salt thereof.

4. The compound according to claim 1, wherein the compound is

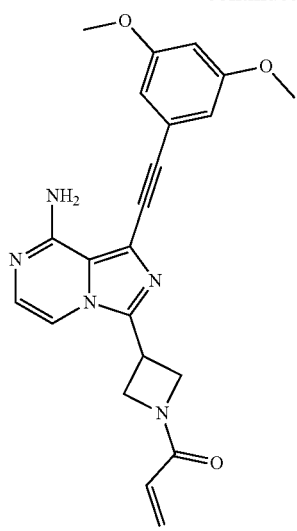

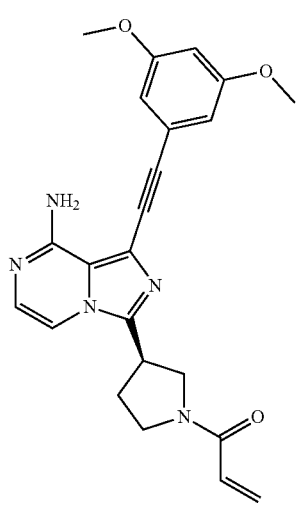

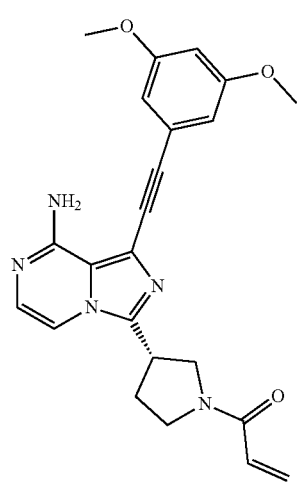

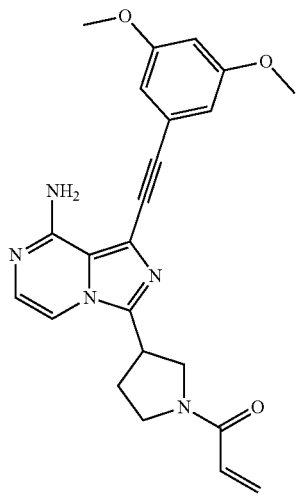

53
-continued
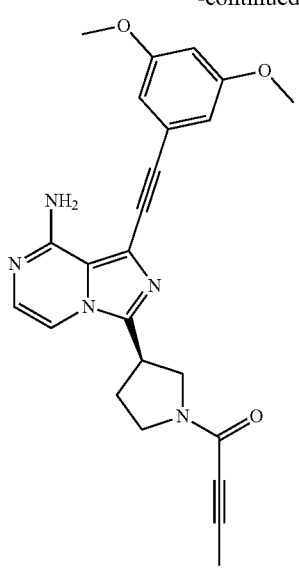
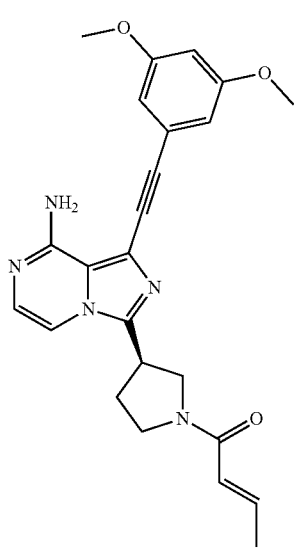
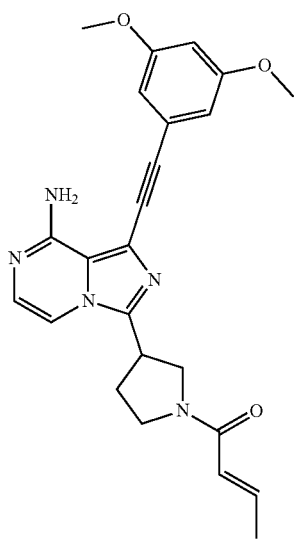
54
-continued
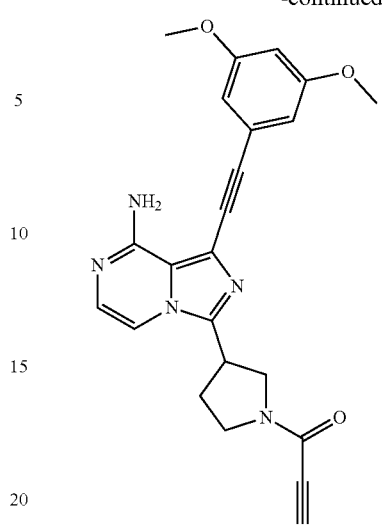
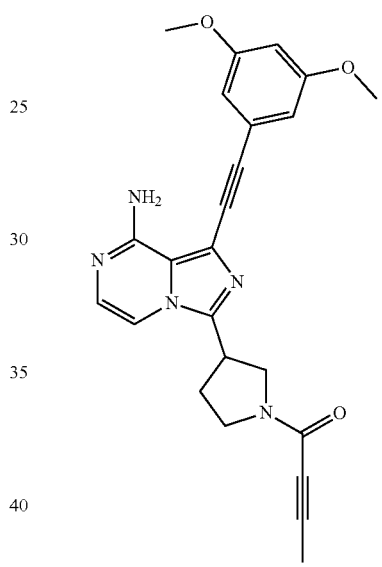
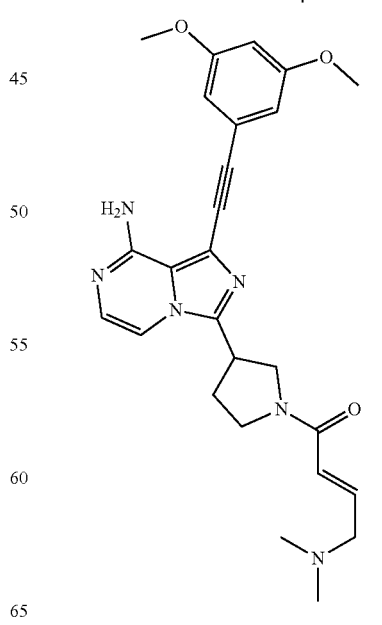

55
-continued
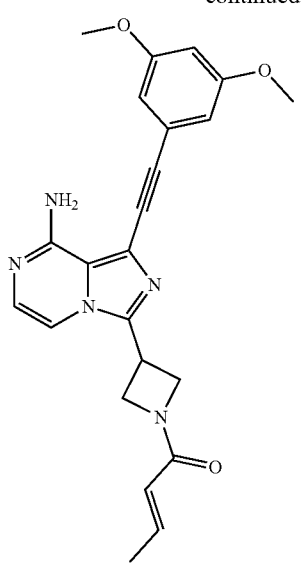
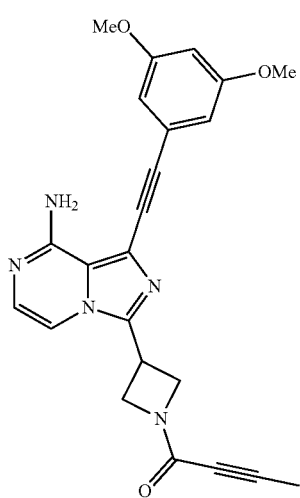
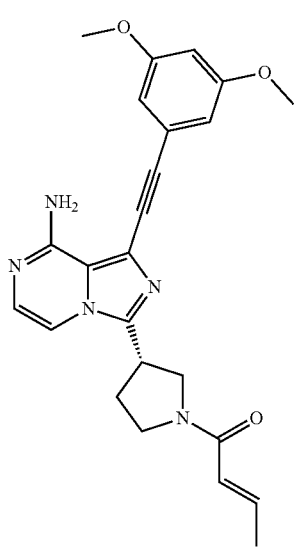
56
-continued
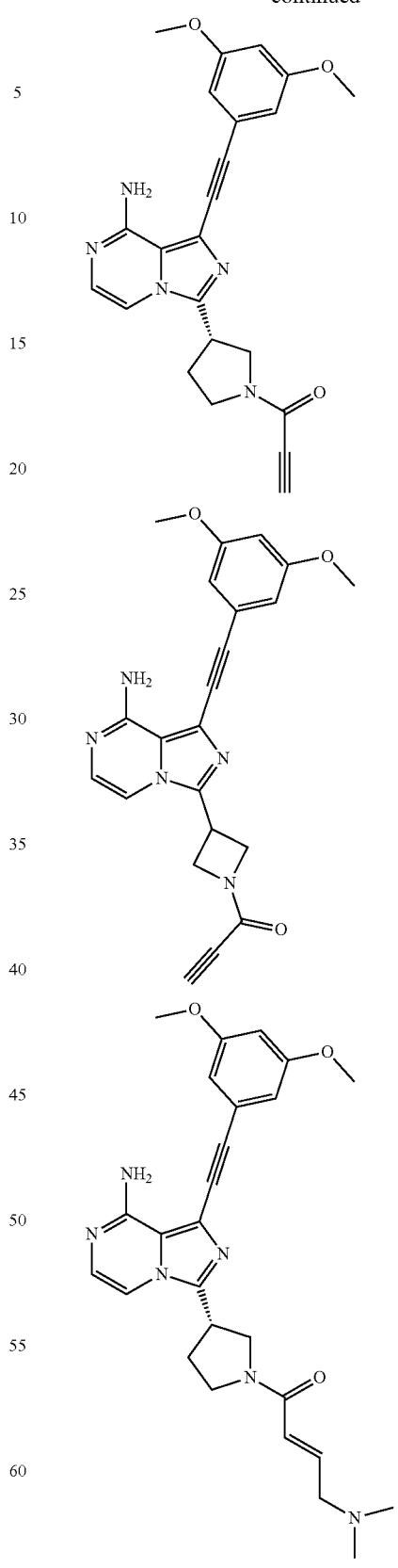

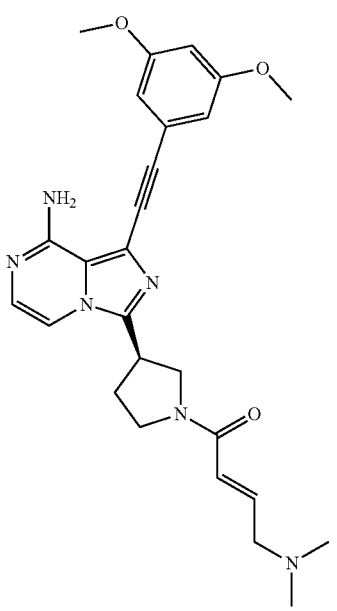

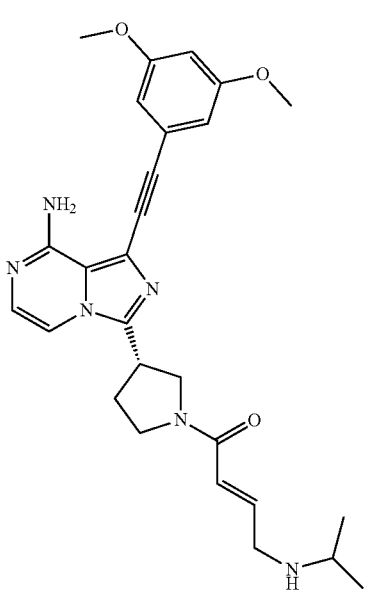

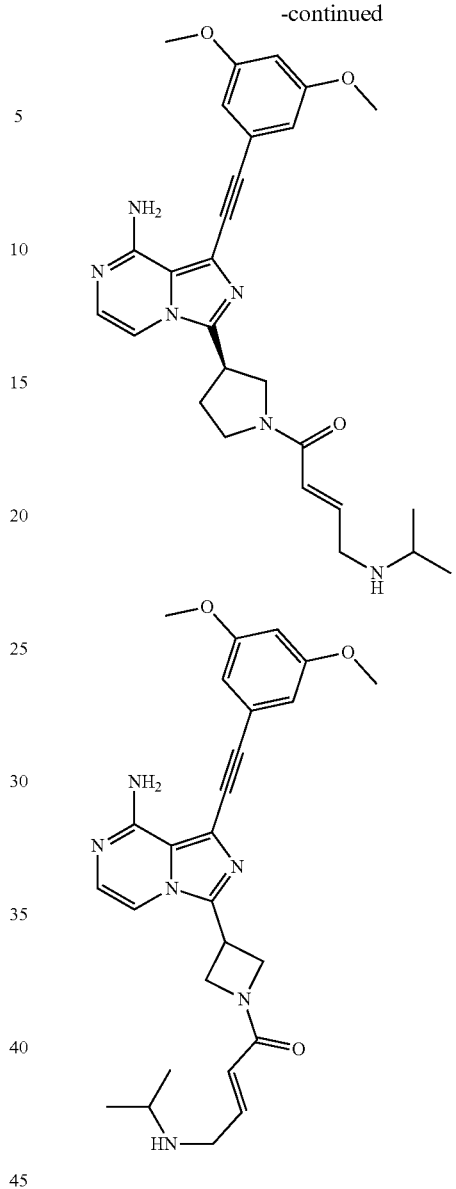

or an isomer, a prodrug, a stable isotopic derivative or a pharmaceutically acceptable salt thereof.

5. A pharmaceutical composition, comprising the compound, or an isomer, a prodrug, a stable isotopic derivative or a pharmaceutically acceptable salt thereof, according to claim 1 and a pharmaceutically acceptable carrier, diluent or excipient.

6. A method for preparing a drug for treating an FGFR-mediated disease, comprising mixing the compound, or an isomer, a prodrug, a stable isotopic derivative or a pharmaceutically acceptable salt thereof, according to claim 1 with a pharmaceutical acceptable carrier, diluent or excipient.

7. A method for treating an FGFR-mediated disease in a patient in need thereof, comprising administering to the patient a therapeutically effective amount of the compound, or an isomer, a prodrug, a stable isotopic derivative or a pharmaceutically acceptable salt thereof, according to claim 1.

8. The method of claim 7, wherein the FGFR-mediated disease is cancer.

9. A pharmaceutical composition, comprising the compound, or an isomer, a prodrug, a stable isotopic derivative or a pharmaceutically acceptable salt thereof, according to claim 2 and a pharmaceutically acceptable carrier, diluent or excipient.

10. A method for preparing a drug for treating an FGFR-mediated disease, comprising mixing the compound, or an isomer, a prodrug, a stable isotopic derivative or a pharmaceutically acceptable salt thereof, according to claim 2 with a pharmaceutical acceptable carrier, diluent or excipient.

11. A method for treating an FGFR-mediated disease in a patient in need thereof, comprising administering to the patient a therapeutically effective amount of the compound, or an isomer, a prodrug, a stable isotopic derivative or a pharmaceutically acceptable salt thereof, according to claim 2.

12. The method of claim 11, wherein the FGFR-mediated disease is cancer.

13. A pharmaceutical composition, comprising the compound, or an isomer, a prodrug, a stable isotopic derivative or a pharmaceutically acceptable salt thereof, according to claim 3 and a pharmaceutically acceptable carrier, diluent or excipient.

14. A method for preparing a drug for treating an FGFR-mediated disease, comprising mixing the compound, or an isomer, a prodrug, a stable isotopic derivative or a pharmaceutically acceptable salt thereof, according to claim 3 with a pharmaceutical acceptable carrier, diluent or excipient.

15. A method for treating an FGFR-mediated disease in a patient in need thereof, comprising administering to the patient a therapeutically effective amount of the compound, or an isomer, a prodrug, a stable isotopic derivative or a pharmaceutically acceptable salt thereof, according to claim 3.

16. The method of claim 15, wherein the FGFR-mediated disease is cancer.

17. A pharmaceutical composition, comprising the compound, or an isomer, a prodrug, a stable isotopic derivative or a pharmaceutically acceptable salt thereof, according to claim 4 and a pharmaceutically acceptable carrier, diluent or excipient.

18. A method for preparing a drug for treating an FGFR-mediated disease, comprising mixing the compound, or an isomer, a prodrug, a stable isotopic derivative or a pharmaceutically acceptable salt thereof, according to claim 4 with a pharmaceutical acceptable carrier, diluent or excipient.

19. A method for treating an FGFR-mediated disease in a patient in need thereof, comprising administering to the patient a therapeutically effective amount of the compound, or an isomer, a prodrug, a stable isotopic derivative or a pharmaceutically acceptable salt thereof, according to claim 4.

20. The method of claim 19, wherein the FGFR-mediated disease is cancer.

\* \* \* \* \*